US006723895B2

(12) United States Patent
DeBonte et al.

(10) Patent No.: US 6,723,895 B2
(45) Date of Patent: Apr. 20, 2004

(54) PLANTS CONTAINING A CYTOSOLIC ACETYL COA-CARBOXYLASE NUCLEIC ACID

(75) Inventors: Lorin R. DeBonte, Ft. Collins, CO (US); Basil S. Shorrosh, Ft. Collins, CO (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 09/839,477

(22) Filed: Apr. 20, 2001

(65) Prior Publication Data

US 2003/0167523 A1 Sep. 4, 2003

Related U.S. Application Data

(60) Provisional application No. 60/198,794, filed on Apr. 20, 2000.

(51) Int. Cl.[7] .......................... A01H 5/00; C12N 15/82
(52) U.S. Cl. ...................... 800/281; 800/287; 800/298; 800/306; 800/312; 435/468
(58) Field of Search .............................. 800/281, 287, 800/298, 306, 312; 435/69.1, 419, 468; 536/23.2, 23.6

(56) References Cited

U.S. PATENT DOCUMENTS

| | | | |
|---|---|---|---|
| 5,498,544 | A | 3/1996 | Gengenbach et al. |
| 5,539,092 | A | 7/1996 | Haselkorn et al. |
| 5,559,220 | A | 9/1996 | Roessler et al. |
| 5,756,290 | A | 5/1998 | Haselkorn et al. |
| 5,792,627 | A | 8/1998 | Haselkorn et al. |
| 5,801,233 | A | 9/1998 | Haselkorn et al. |
| 5,854,420 | A | 12/1998 | Ashton et al. |
| 5,910,626 | A | 6/1999 | Haselkorn et al. |
| 5,925,805 | A | 7/1999 | Ohlrogge et al. |
| 5,962,767 | A | 10/1999 | Ohlrogge et al. |
| 5,972,644 | A | 10/1999 | Haselkorn et al. |

OTHER PUBLICATIONS

Ashton et al., "Molecular cloning of two different cDNAs for maize acetyl CoA carboxylase," *Plant Mol. Biol.*, 1994, 24:35–49.
Charles and Cherry, "Purification and Characterization of Acetyl–CoA Carboxylase from Developing Soybean Seeds," *Phytochemistry*, 1986, 25(5):1067–1071.
DeHaye et al., "Kinetics of the two forms of acetyl–CoA carboxylase from *Pisum sativum*," *Eur. J. Biochem.*, 1994, 225:1113–1123.
Egin–Bühler and Ebel, "Improved Purification and Further Characterization of Acetyl–CoA Carboxylase from Cultured Cells of Parsley (*Petroselinum hortense*)," *Eur. J. Biochem.*, 1983, 133:335–339.
Egli et al., "Characterization of Maize Acetyl–Coenzyme A Carboxylase," *Plant Physiol.*, 1993, 101:499–506.
Elborough et al., "Isolation of cDNA's from *Brassica napus* encoding the biotin–binding and transcarboxylase domains of acetyl–CoA carboxylase: assignment of the domain structure in a full–length *Arabidopsis thaliana* genomic clone," *Biochem. J.*, 1994, 301:599–605.
Gornicki and Haselkorn, "Wheat acetyl–CoA carboxylase," *Plant Mol. Biol.*, 1993, 22:547–552.
Gornicki et al., "Wheat acetyl–coenzyme A carboxylase: cDNA and protein structure," *Proc. Natl. Acad. Sci. USA*, 1994, 91:6860–6864.
Ha et al., "Cloning of human acetyl–CoA carboxylase cDNA," *Eur. J. Biochem.*, 1994, 219:297–306.
Nikolau and Hawke, "Purification and Characterization of Maize Leaf Acetyl–coenzyme A Carboxylase," *Arch. Biochem. Biophys.*, 1984, 228:86–96.
Page et al., "Acetyl–CoA carboxylase exerts strong flux over lipid synthesis in plants," *Biochim. Biophys. Acta*, 1994, 1210:369–372.
Pollard and Stumpf, "Biosynthesis of $C_{20}$ and $C_{22}$ Fatty Acids by Developing Seeds of *Limnanthes alba*," *Plant Physiol.*, 1980, 66:649–655.
Post–Beittenmiller et al., "Regulation of Plant Fatty Acid Biosynthesis," *Plant Physiol.*, 1992, 100:923–930.
Roesler et al., "Structure and Expression of an Arabidopsis Acetyl–Coenzyme A Carboxylase Gene," *Plant Physiol.*, 1994, 105:611–617.
Roesler et al., "Co–purification, co–immunoprecipitation, and coordinate expression of acetyl–coenzyme A carboxylase activity, biotin carboxylase, and biotin carboxyl carrier protein of higher plants," *Planta*, 1996, 198:517–525.
Roesler et al., "Targeting of the Arabidopsis Homomeric Acetyl–Coenzyme A Carboxylase to Plastids of Rapeseeds," *Plant Physiol.*, 1997, 113:75–81.
Roessler and Ohlrogge, "Cloning and Characterization of the Gene That Encodes Acetyl–coenzyme A Carboxylase in the Alga *Cyclotella cryptica*," *J. Biol. Chem.*, 1993, 268(26):19254–19259.
Schulte et al., "A Gene Encoding Acetyl–Coenzyme A Carboxylase from *Brassica napus*," *Plant Physiol.*, 1994, 106:793–794.
Schulte et al., "Multi–functional acetyl–CoA carboxylase from *Brassica napus* is encoded by a multi–gene family: Indication for plastidic localization of at least one isoform," *Proc. Natl. Acad. Sci. USA*, 1997, 94:3465–3470.
Shorrosh et al., "Molecular cloning, characterization, and elicitation of acetyl–CoA carboxylase from alfalfa," *Proc. Natl. Acad. Sci. USA*, 1994, 91:4323–4327.
Shorrosh et al., "Structural Analysis, Plastid Localization, and Expression of the Biotin Carboxylase Subunit of Acetyl–Coenzyme A Carboxylase from Tobacco," *Plant Physiol.*, 1995, 108:805–812.

*Primary Examiner*—Elizabeth F. McElwain
(74) *Attorney, Agent, or Firm*—Fish & Richardson P.C., P.A.

(57) ABSTRACT

Plants are disclosed that contain a recombinant nucleic acid construct comprising a nucleic acid encoding a cytosolic acetyl coA-carboxylase (ACCase) operably linked to a promoter. Seeds produced from such plants exhibit statistically significantly increased oil content as compared to seeds produced by a corresponding plant lacking the nucleic acid encoding the ACCase. Methods of producing seeds exhibiting statistically significantly increased oil content are also disclosed.

22 Claims, 9 Drawing Sheets

```
atggcttcctcagttctttcctctgcagcagttgccacccgcagcaatgttgctcaagct
 M  A  S  S  V  L  S  S  A  A  V  A  T  R  S  N  V  A  Q  A aacatggttgcacctttcactggccttaagtcagctgcctcattccctgtttcaaggaag
 N  M  V  A  P  F  T  G  L  K  S  A  A  S  F  P  V  S  R  K caaaaccttgacatcacttccattgccagcaacggcggaagagtgcaatgcatgcaggtg
 Q  N  L  D  I  T  S  I  A  S  N  G  G  R  V  Q  C  M  Q  V tggccaccaattaacaagaagtcc        (SEQ ID NO:3)
 W  P  P  I  N  K  K  S         (SEQ ID NO:4)
```

Figure 1

```
atggctagcgtgggccgtggaaatggatatttaaacagtgtgctaccgagtaggcaccctgctactacaaccgaa
 M  A  S  V  G  R  N  G  Y  L  N  S  V  L  P  S  R  H  P  A  T  T  T  E gtagatgaatactgcaatgcccttggaggaaacaagccgattcatagcatattgattgcaaacaatggaatggca
 V  D  E  Y  C  N  A  L  G  G  N  K  P  I  H  S  I  L  I  A  N  N  G  M  A gcagtcaagtttatacgtagtgttaggagttgggcttacgagacatttggcacggaaaaagctatcttgttggtt
 A  V  K  F  I  R  S  V  R  S  W  A  Y  E  T  F  G  T  E  K  A  I  L  L  V gccatggcaactccagaggatatgagaatcaatgcagaacatatcagaatagccgatcaatttgtggaagtacct
 A  M  A  T  P  E  D  M  R  I  N  A  E  H  I  R  I  A  D  Q  F  V  E  V  P ggtgggaccaataacaataactacgccaatgtgcagcttattctagagattgctgagataactcacgttgatgcg
 G  G  T  N  N  N  Y  A  N  V  Q  L  I  L  E  I  A  E  I  T  H  V  D  A gtgtggcctggttggggtcatgcatcagaaaatcctgagcttccagatgcattaaaagcaagggaattgtattc
 V  W  P  G  W  G  H  A  S  E  N  P  E  L  P  D  A  L  K  A  K  G  I  V  F cttggacctcctgctatatctatggcagcattgggagacaaaattggttcctcgttgattgctcaggcagcagaa
 L  G  P  P  A  I  S  M  A  A  L  G  D  K  I  G  S  S  L  I  A  Q  A  A  E gttccaacccttccatggagtggttctcatgtgaaaattcctccagaaagtgacttgattactattcctgatgaa
 V  P  T  L  P  W  S  G  S  H  V  K  I  P  P  E  S  D  L  I  T  I  P  D  E atttaccgtgcagcatgtgtttatacaacagaagaagcaattgcaagttgtcaagtagtaggttaccctgcaatg
 I  Y  R  A  A  C  V  Y  T  T  E  E  A  I  A  S  C  Q  V  V  G  Y  P  A  M attaaggcatcttggggtggtggcggcaaaggcataagaaaggttcataatgatgatgaggttagggcattgttc
 I  K  A  S  W  G  G  G  G  K  G  I  R  K  V  H  N  D  D  E  V  R  A  L  F aagcaagttcaaggtgaagtaccaggctcacctatatttataatgaaagttgcttcccagagccgacatcttgaa
 K  Q  V  Q  G  E  V  P  G  S  P  I  F  I  M  K  V  A  S  Q  S  R  H  L  E gtccaattgatttgcgatcagcacggaaatttttgcagcattgcacagccgtgattgtagtgttcaaagaaggcat
 V  Q  L  I  C  D  Q  H  G  N  F  A  A  L  H  S  R  D  C  S  V  Q  R  R  H caaaagattattgaagagggtcccattactgtagcacctccagaaacggtgaaagaacttgaacaggcggctaga
 Q  K  I  I  E  E  G  P  I  T  V  A  P  P  E  T  V  K  E  L  E  Q  A  A  R agattagctaaatctgtaaattatgtgggggcagctaccgttgagtatctttatagcatggaaactggcgagtac
 R  L  A  K  S  V  N  Y  V  G  A  A  T  V  E  Y  L  Y  S  M  E  T  G  E  Y tacttttttagagttgaaccccgactacaggttgagcatcctgttactgaatggatagctgagataaatctgcca
 Y  F  L  E  L  N  P  R  L  Q  V  E  H  P  V  T  E  W  I  A  E  I  N  L  P gcagcacaagttgcagttgggatggcatcccactctggcaaattcctgagattaggcgtttctatgggatggaa
 A  A  Q  V  A  V  G  M  G  I  P  L  W  Q  I  P  E  I  R  R  F  Y  G  M  E catggtgggggaaatgatggttggaagaaaacatcagtgttagctacccctttttgattttgacgaagcacaatct
 H  G  G  G  N  D  G  W  K  K  T  S  V  L  A  T  P  F  D  F  D  E  A  Q  S
```

Figure 4-1

```
acaaagccgaaaggtcattgtgtggctgtacgagtcaccagtgaggaccccgatgatggttttacgcctacagga
 T  K  P  K  G  H  C  V  A  V  R  V  T  S  E  D  P  D  D  G  F  T  P  T  G ggaaaagtgcaggagctcagctttaaaagcaagccaaatgtgtgggcttatttctctgttaagtccggaggagga
 G  K  V  Q  E  L  S  F  K  S  K  P  N  V  W  A  Y  F  S  V  K  S  G  G attcatgaattctcagattctcaatttggacatgttttgcgtttggagaatctagagctttagcaattgcaaat
 I  H  E  F  S  D  S  Q  F  G  H  V  F  A  F  G  E  S  R  A  L  A  I  A  N atggtactggggttgaaggaaattcaaattcgaggagaaattcgtaccaacgttgattacacaattgatcttctg
 M  V  L  G  L  K  E  I  Q  I  R  G  E  I  R  T  N  V  D  Y  T  I  D  L  L aatgcttcagactacagagacaacaaaattcacacaggatggctagacagtagaattgcaatgcgggttagagca
 N  A  S  D  Y  R  D  N  K  I  H  T  G  W  L  D  S  R  I  A  M  R  V  R  A gagaggcctccctggtatctgtctgttgttggtggggcactctataaagcttctgccagcagtgcagctttagtt
 E  R  P  P  W  Y  L  S  V  V  G  G  A  L  Y  K  A  S  A  S  S  A  A  L  V tcggactatgttggctatcttgaaaaggggcaaatccctcccaagcacatttctcttgtccattctcaagtttct
 S  D  Y  V  G  Y  L  E  K  G  Q  I  P  P  K  H  I  S  L  V  H  S  Q  V  S ttgagcattgaaggaagcaaatacacgattgacatggtacgaggaggacctggaagttacaaattgaaattgaat
 L  S  I  E  G  S  K  Y  T  I  D  M  V  R  G  G  P  G  S  Y  K  L  K  L  N caatcggagatagaagcggagatacacactttacgtgatggaggtttgctaatgcagttggatggaaacagtcat
 Q  S  E  I  E  A  E  I  H  T  L  R  D  G  G  L  L  M  Q  L  D  G  N  S  H gtaatatatgcagaggaagaagcagctggaactcggcttttaatagatggaaggacttgcttgcttcagaatgat
 V  I  Y  A  E  E  A  A  G  T  R  L  L  I  D  G  R  T  C  L  L  Q  N  D gacgatccatcaaagttaattggagagacaccgtgcaagcttctgagatatttggttgcggatgatagtcagatt
 D  D  P  S  K  L  I  G  E  T  P  C  K  L  L  R  Y  L  V  A  D  D  S  Q  I gatgcagacacaccatatgctgaagttgaggtcatgaagatgtgcatgcctcttctttcccctgcttctggaatt
 D  A  D  T  P  Y  A  E  V  E  V  M  K  M  C  M  P  L  L  S  P  A  S  G  I attcatttcagaatggctgaaggtcaagccatgcaggctggtgaacttatagcaaagcttgatctagatgatggt
 I  H  F  R  M  A  E  G  Q  A  M  Q  A  G  E  L  I  A  K  L  D  L  D  D  G tctgcagtaaggaaggcagaacccttcactgggagcttccctatcctgggccctcctactgcaatttcaggtaaa
 S  A  V  R  K  A  E  P  F  T  G  S  F  P  I  L  G  P  P  T  A  I  S  G  K gttcatcagaaatgtgcagcaagcttaaacgctgcacggatgattcttgctggctatgagcacaacattgatgaa
 V  H  Q  K  C  A  A  S  L  N  A  A  R  M  I  L  A  G  Y  E  H  N  I  D  E gttgtggtcaaaagtttgctcaattgccttgacagccctgaactgcctttccttcaatggcaagagtgctttgca
 V  V  V  K  S  L  L  N  C  L  D  S  P  E  L  P  F  L  Q  W  Q  E  C  F  A gttttggcaacccgtcttcccaaagatcttagaaacgagttggaagctaaatataaggagttcgaaattatttca
 V  L  A  T  R  L  P  K  D  L  R  N  E  L  E  A  K  Y  K  E  F  E  I  I  S
```

*Figure 4-2*

```
agctcccaaactattgatttccctgccaaattattgaaggcaatccttgaagctcatctttcctcctgtcctgaa
 S  S  Q  T  I  D  F  P  A  K  L  L  K  A  I  L  E  A  H  L  S  S  C  P  E aacgaaaaaggagccttagaaagactagttgaaccgctgacaagtcttgtaaagtcttatgagggtggaagagag
 N  E  K  G  A  L  E  R  L  V  E  P  L  T  S  L  V  K  S  Y  E  G  G  R  E agccatgctcataaaattgttcaatctctatttgaagagtatctttcagttgaagaactattcagtgataatata
 S  H  A  H  K  I  V  Q  S  L  F  E  E  Y  L  S  V  E  E  L  F  S  D  N  I caggctgatgtaattgaacgactccgtcttcaatacaagaaagatttgttgaagattgtagatattgtgctctct
 Q  A  D  V  I  E  R  L  R  L  Q  Y  K  K  D  L  L  K  I  V  D  I  V  L  S catcagggtgtcaagagcaaaaacaagctgatactgcgactaatggataaactggtttaccctaatcctgctgcc
 H  Q  G  V  K  S  K  N  K  L  I  L  R  L  M  D  K  L  V  Y  P  N  P  A  A tatagggatcaattaatccgattctcccaactcaaccatatagtttattctgagttggctcttaaggcaagtcaa
 Y  R  D  Q  L  I  R  F  S  Q  L  N  H  I  V  Y  S  E  L  A  L  K  A  S  Q ctgttggagcaaactaaactcagtgaacttcgatccagcattgctagaagtctttctgaactagaaatgtttacc
 L  L  E  Q  T  K  L  S  E  L  R  S  S  I  A  R  S  L  S  E  L  E  M  F  T gaggatggtgaaaatattgatactccgaagaggaagagtgccattaatgacagaatggaggaccttgtgagcgct
 E  D  G  E  N  I  D  T  P  K  R  K  S  A  I  N  D  R  M  E  D  L  V  S  A cctttggctgttgaagatgcccttgttggtttatttgatcacagcgatcacacccttcaaaggagagttgttgaa
 P  L  A  V  E  D  A  L  V  G  L  F  D  H  S  D  H  T  L  Q  R  R  V  V  E acttatatccgtaggctctatcagccatatcttgtcaaagatagcatcaggatgcagtggcacagatctggcctt
 T  Y  I  R  R  L  Y  Q  P  Y  L  V  K  D  S  I  R  M  Q  W  H  R  S  G  L attgctacatgggaattcttagaagaatacgttgaacggaagaatggggttgaagacaaaacactggtggagaaa
 I  A  T  W  E  F  L  E  E  Y  V  E  R  K  N  G  V  E  D  K  T  L  V  E  K catagtgagaagaaatggggagtgatggttgtaattaaatctcttcagttttgccagcaattatcagtgctgca
 H  S  E  K  K  W  G  V  M  V  V  I  K  S  L  Q  F  L  P  A  I  I  S  A  A ttaagagaagcaaccaataactttcacgatcctcttaaaagtggttctggtgactcaagtaaccatggtaatatg
 L  R  E  A  T  N  N  F  H  D  P  L  K  S  G  S  G  D  S  S  N  H  G  N  M atgcatattggattagtggggatcaacaaccaaatgagtttacttcaagacagtggtgatgaggatcaggctcaa
 M  H  I  G  L  V  G  I  N  N  Q  M  S  L  L  Q  D  S  G  D  E  D  Q  A  Q gaaagaattgataagttggccaaaatactcagagagcaggaaatagggtccataatacatgctgcaggtgttgga
 E  R  I  D  K  L  A  K  I  L  R  E  Q  E  I  G  S  I  I  H  A  A  G  V  G gatattagctgtatcatacagagggatgaaggcgtgctccaatgaggcattcctttcactggtcatctgaaaag
 D  I  S  C  I  I  Q  R  D  E  G  R  A  P  M  R  H  S  F  H  W  S  S  E  K ctatattatgtagaggaaccattgttgctccatcttgaacctcccctatccatttatcttgaactggacaagctt
 L  Y  Y  V  E  E  P  L  L  L  H  L  E  P  P  L  S  I  Y  L  E  L  D  K  L
```

*Figure 4-3*

```
aagtgctatgaaaatattcgctatacaccatcccgagatcgtcaatggcacctctacacagttgtggataccaag
 K   C   Y   E   N   I   R   Y   T   P   S   R   D   R   Q   W   H   L   Y   T   V   V   D   T   K ccacaaccaattcaaagaatgtttcttcgaacacttatcagacagccaaccacaaatgaaggatactcttcttat
 P   Q   P   I   Q   R   M   F   L   R   T   L   I   R   Q   P   T   T   N   E   G   Y   S   S   Y caaagactggatgcagaaacgtcccgtacccaattggctatgtcttatacttcaaggagcattttaggtcccta
 Q   R   L   D   A   E   T   S   R   T   Q   L   A   M   S   Y   T   S   R   S   I   F   R   S   L atgggcgcaatggaggagttggaacttaactcacacaataccaccatcaaatctgaacatgctcatatgtacctc
 M   G   A   M   E   E   L   E   L   N   S   H   N   T   T   I   K   S   E   H   A   H   M   Y   L tatatcatacgcgagcagcaaatagatgatcttgtgccttattccaagaaaattaacatagaagctggccaagaa
 Y   I   I   R   E   Q   Q   I   D   D   L   V   P   Y   S   K   K   I   N   I   E   A   G   Q   E gaaacaacagttgaggcaatcttggaagaactggcacaggaaatccattcctctgttggtgtaagaatgcacaga
 E   T   T   V   E   A   I   L   E   E   L   A   Q   E   I   H   S   S   V   G   V   R   M   H   R ttaggcgttttcgtgtgggaaatcaagctctggattacagcatgtggacaggcaaatggtgcttggagggtcatt
 L   G   V   F   V   W   E   I   K   L   W   I   T   A   C   G   Q   A   N   G   A   W   R   V   I gtaaacaatgtgactggtcatacatgcactgtacatatatatcgagagatggaggatgccaccactcataaagtg
 V   N   N   V   T   G   H   T   C   T   V   H   I   Y   R   E   M   E   D   A   T   T   H   K   V gtctacagttcagtcactgtaaagggtccgttgcatggtgtaccggtgaatgaaaactatcaacctttgggaggt
 V   Y   S   S   V   T   V   K   G   P   L   H   G   V   P   V   N   E   N   Y   Q   P   L   G   G attgaccgaaaacgtcttgcagcgagaaagaacagcaccacatactgctatgatttccccccttgcatttcaaaca
 I   D   R   K   R   L   A   A   R   K   N   S   T   T   Y   C   Y   D   F   P   L   A   F   Q   T tccttggaacagtcctggtcaatacagcagacaggaattcaaagagctaatgataaggatctcctaaaagtaaca
 S   L   E   Q   S   W   S   I   Q   Q   T   G   I   Q   R   A   N   D   K   D   L   L   K   V   T gagcttaaattttccgaaaaagctggtagttggggtacttctcttgttcctgcagagcgtcttcctggactcaat
 E   L   K   F   S   E   K   A   G   S   W   G   T   S   L   V   P   A   E   R   L   P   G   L   N gatgttggcatggtagcctggttgatggaaatgtgtacgcctaaattcccatctggaaggacaatattggttgtt
 D   V   G   M   V   A   W   L   M   E   M   C   T   P   K   F   P   S   G   R   T   I   L   V   V tcaaacgatgtgaccttcaaggccgggtcttttggcccaagagaggatgcattctttagagcagtaactgatctt
 S   N   D   V   T   F   K   A   G   S   F   G   P   R   E   D   A   F   F   R   A   V   T   D   L gcctgtgcaaagaaaatacctttaatttacttggcagcaaattctggtgcccgtttaggtgttgccgaggaagtc
 A   C   A   K   K   I   P   L   I   Y   L   A   A   N   S   G   A   R   L   G   V   A   E   E   V aaagcttgtttcaaagttggttggtctgaggaatctaaacctgaacatggttttcagtatgtatatttaacacct
 K   A   C   F   K   V   G   W   S   E   E   S   K   P   E   H   G   F   Q   Y   V   Y   L   T   P gaggattatgctcgaatcggatcatcagtgatggcacatgaattaaagcttgaaagtggagaaaccagatgggtt
 E   D   Y   A   R   I   G   S   S   V   M   A   H   E   L   K   L   E   S   G   E   T   R   W   V
```

Figure 4-4

```
atagataccattgttggcaaagaagatggactgggagttgaaaacttgagtggtagtggggccattgccggtgcc
 I   D   T   I   V   G   K   E   D   G   L   G   V   E   N   L   S   G   S   G   A   I   A   G   A tattcaagggcatacaaggaaacctttacattgacatatgttaccggtaggactgttggaattggtgcttatctt
 Y   S   R   A   Y   K   E   T   F   T   L   T   Y   V   T   G   R   T   V   G   I   G   A   Y   L gctaggcttgggatgaggtgcatacagaggcttgatcaacctataattcttaccgggttttcagcattaaacaaa
 A   R   L   G   M   R   C   I   Q   R   L   D   Q   P   I   I   L   T   G   F   S   A   L   N   K cttcttggtagggaggtgtacagctctcacatgcaacttggtggaccgaaaatcatggcaacaaatggagtcgtt
 L   L   G   R   E   V   Y   S   S   H   M   Q   L   G   G   P   K   I   M   A   T   N   G   V   V catctcacagtttcggacgaccttgaaggcgtttcttctatttttgaagtggcttagctacgttccttctcatgta
 H   L   T   V   S   D   D   L   E   G   V   S   S   I   L   K   W   L   S   Y   V   P   S   H   V ggtggtgcacttcccattgtaaagccccttgatcccccagagagggaagtggagtatttaccggaaaattcatgc
 G   G   A   L   P   I   V   K   P   L   D   P   P   E   R   E   V   E   Y   L   P   E   N   S   C gatcctcgtgctgccatttccggaactctggatgttaatggaaagtggctgggaggcattttttgacaaggacagc
 D   P   R   A   A   I   S   G   T   L   D   V   N   G   K   W   L   G   G   I   F   D   K   D   S tttgtggagacactagaaggatgggctagaacagttgttacaggaagggcaaagcttggaggaatccctgtggga
 F   V   E   T   L   E   G   W   A   R   T   V   V   T   G   R   A   K   L   G   G   I   P   V   G attgttgcggtggaaacacaaacagttatgcaaataatacctgctgatccaggtcaacttgattctcacgagagg
 I   V   A   V   E   T   Q   T   V   M   Q   I   I   P   A   D   P   G   Q   L   D   S   H   E   R gttgttcctcaagccgggcaggtgtggtttcctgattctgcgaccaagacggcccaagcgatattggatttcaac
 V   V   P   Q   A   G   Q   V   W   F   P   D   S   A   T   K   T   A   Q   A   I   L   D   F   N agagaagaactcccacttttcattatcgcaaactggagaggcttttcaggtggacaaagggaccttttgaagga
 R   E   E   L   P   L   F   I   I   A   N   W   R   G   F   S   G   G   Q   R   D   L   F   E   G attcttcaggctggttcgactattgtggagaaccttaggacatacaaacagcccatatttgtatacattccaatg
 I   L   Q   A   G   S   T   I   V   E   N   L   R   T   Y   K   Q   P   I   F   V   Y   I   P   M atgggtgaactccgaggcggggcttggttgttgtcgacagccgaatcaactcagaccacattgaaatgtatgct
 M   G   E   L   R   G   G   A   W   V   V   V   D   S   R   I   N   S   D   H   I   E   M   Y   A gagcgaacggccaaaggtaacgtccttgagccggaaggaatgattgaaatcaaatttagaacaagagaattgttg
 E   R   T   A   K   G   N   V   L   E   P   E   G   M   I   E   I   K   F   R   T   R   E   L   L gagtgtatgagaagacttgatcaacaattgattaatttgaaggaaaaactttctgaagccaagagtaacaaggac
 E   C   M   R   R   L   D   Q   Q   L   I   N   L   K   E   K   L   S   E   A   K   S   N   K   D tatggtgcatatgattctctgcagcagcagattagattccgtgagaaacagcttttgcctttgtatactcagata
 Y   G   A   Y   D   S   L   Q   Q   Q   I   R   F   R   E   K   Q   L   L   P   L   Y   T   Q   I gctacaaaatttgctgaactccatgatacttcattaagaatgaaagcaaagggtgtaatcagagaagttcttgat
 A   T   K   F   A   E   L   H   D   T   S   L   R   M   K   A   K   G   V   I   R   E   V   L   D
```

*Figure 4-5*

```
tggcgtaagtcgcgttctgtcttctatcagagactgcacaggagaatcggtgagcactcactgatcaacatcgtg
 W  R  K  S  R  S  V  F  Y  Q  R  L  H  R  R  I  G  E  H  S  L  I  N  I  V agagatgctgctggtgaccaattgtcatatgtttctgccatgaacttgctcaaagaatggtatctgaattctgat
 R  D  A  A  G  D  Q  L  S  Y  V  S  A  M  N  L  L  K  E  W  Y  L  N  S  D atcgccaaaggtagagaagatgcttggttggacgatgaagccttcttcagatggagggatgatccagcaaactac
 I  A  K  G  R  E  D  A  W  L  D  D  E  A  F  F  R  W  R  D  D  P  A  N  Y gaggataaactaaaggaattgcgcgtccagagactgttgcttcagttgacaaatattggcgactcggctctagat
 E  D  K  L  K  E  L  R  V  Q  R  L  L  L  Q  L  T  N  I  G  D  S  A  L  D ttacaagctctacctcaaggtcttgccgcccttttaagcaagttggaagcatcaagtcgcgataagttgatcagt
 L  Q  A  L  P  Q  G  L  A  A  L  L  S  K  L  E  A  S  S  R  D  K  L  I  S gaacttcgcaaagtactcggttagtagacagtgaatgctcctgtgatctgcccatgcactcatgttgtagtgttc
 E  L  R  K  V  L  G           (SEQ ID NO:8)

acgtcgttgatacatgaccatatagaaatgtatccattttacgatgttatcatcaaagtagcagcatccctcgga aaatggactttcacttgagggatcaactgtaaatgacttcggtcttggatagatatttaatttatgcagttagag gatcataaccagcatcaccatgtttggtctatttatttgctggttgattgattctttgcgtgtatctgaataaac atgtaataatttgtaacattgattattttttatgaaaaacaaagttttgggcactccttttataaaaaaaaaaaa aagaattcctgcagcccgggggatcc        (SEQ ID NO:7)
```

*Figure 4-6*

PLANTS CONTAINING A CYTOSOLIC ACETYL COA-CARBOXYLASE NUCLEIC ACID

CROSS-REFERENCE TO RELATED APPLICATIONS

This application claims priority under 35 U.S.C. §119(e) of U.S. provisional application Ser. No. 60/198,794, filed Apr. 20, 2000.

TECHNICAL FIELD

This invention relates to oilseed plants, and more particularly to plants containing a nucleic acid encoding a cytosolic acetyl coA-carboxylase (ACCase) enzyme.

BACKGROUND

Acetyl-CoA carboxylase [ACCase; EC 6.4.1.2] catalyzes the first committed step in fatty acid biosynthesis by converting acetyl-CoA to malonyl-CoA. In plants, a multisubunit (MS) form and a multifunctional (MF) form of ACCase have been identified. The MS form is composed of dissociable subunits of different sizes, including a biotin carboxyl carrier protein (BCCP), $\alpha$- and $\beta$-carboxyltransferases ($\alpha$-CT and $\beta$-CT, respectively), and a biotin carboxylase (BC). The MS form is present in plastids of dicotyledenous and of non-Gramineae monocotyledenous plants and is primarily involved in the biosynthesis of fatty acids.

The MF form of a plant ACCase is similar to mammalian ACCase (and is sometimes designated "eukaryotic" or "cytosolic" ACCase), in that it is a MF polypeptide with a molecular weight of more than 200 kDa. The MF form of ACCase from plants contains BCCP, BC, $\alpha$-CT and $\beta$-CT functional domains in a single polypeptide. MF ACCase is most likely present in the cytosol of all plant species and in the chloroplasts of Gramineae plants. Plant MF ACCase is involved in the biosynthesis of very long chain fatty acids, flavonoids, and in the malonation of amino acids and aminocyclopropane-1-carboxylate (a precursor to ethylene). Antisense nucleic acids against an ME ACCase have been introduced into *Brassica napus* (White et al., 1998, in *Adv. in Plant Lipid Res.*, pp. 62–66, eds., Sánchez, J., Cerdá-Olmedo, E. & Martinez-Horce, E., Universidad De Sevilla, Spain) and an Arabidopsis genomic DNA encoding an MF ACCase under the control of a napin seed-specific promoter and linked to a small subunit (ss) Rubisco transit peptide was introduced into *B. napus* (Roesler et al., 1997, *Plant Physiol.*, 113:75–81; U.S. Pat. No. 5,925,805).

SUMMARY

Plants have been engineered to express a nucleic acid encoding an MF acetyl coA-carboxylase (ACCase), hereinafter referred to as cytosolic ACCase. Oil content was significantly increased in plants containing the cytosolic ACCase coding sequences.

In general, the invention feature plants containing a nucleic acid construct carrying a nucleic acid encoding a cytosolic ACCase operably linked to a promoter and lacking a transit peptide. This plant produces seeds that exhibit a statistically significant increase in oil content as compared to seeds produced by a corresponding plant lacking such a construct.

The invention additionally features plants containing a nucleic acid construct carrying a nucleic acid encoding a cytosolic ACCase lacking introns operably linked to a promoter. This plant produces seeds that exhibit a statistically significant increase in oil content as compared to seeds produced by a corresponding plant lacking such a construct.

The invention also features methods of producing a transgenic plant. This method includes selecting progeny transgenic plants of a plant containing a nucleic acid construct carrying a nucleic acid encoding a cytosolic ACCase operably linked to a promoter. Following at least one generation of selection, one or more of the progeny transgenic plants produce seeds exhibiting a statistically significant increase in oil content as compared to seeds produced by a corresponding plant lacking such a construct.

The invention further features methods of producing a plant by introducing a construct carrying a nucleic acid encoding a cytosolic ACCase operably linked to a promoter into one or more plants. Progeny of these plants, following at least one generation of selection, produce seeds that exhibit a statistically significant increase in oil content when compared to seeds produced by a corresponding plant lacking such a construct.

Yet another feature of the invention are methods of increasing the oil content in seeds by creating a plant containing a nucleic acid construct carrying a gene encoding a cytosolic ACCase operably linked to a promoter, and selecting progeny of the plant that exhibit a statistically significant increase in oil content in seeds as compared to seeds produced by a corresponding plant lacking such a construct.

Additionally featured in the invention are seeds produced by the above-described plants, and progeny of those plants, wherein the progeny produce seeds that exhibit a statistically significant increase in oil content when compared to seeds produced by the progeny of plants lacking such a construct.

Typically, the increase in oil content is from about 5% to about 25% on a dry weight basis. The above-described selection steps can include selecting progeny that contain the nucleic acid construct. Generally, soybean plants or Brassica plants, for example, *Brassica napus, B. rapa, B. juncea, B. carinata, B. nigra* and *B. oleracea* are useful in the invention.

Still yet another feature of the invention is a nucleic acid construct carrying a cytosolic ACCase coding sequence operably linked to a promoter but lacking a transit peptide and a nucleic acid construct carrying a cytosolic ACCase coding sequence lacking introns operably linked to a promoter.

A promoter included in a construct of the invention can be a cauliflower mosaic virus (CaMV) 35S promoter. Unless otherwise indicated, the ACCase constructs described herein may or may not include nucleic acid sequences encoding a transit peptide operably linked to the nucleic acid sequences encoding the cytosolic ACCase. An example of a transit peptide is a tobacco small subunit Rubisco transit peptide. In addition, a nucleic acid encoding a cytosolic ACCase can encode a plant cytosolic ACCase, for example, an alfalfa cytosolic ACCase. Further and unless otherwise indicated, a nucleic acid encoding the ACCase can lack introns.

Unless otherwise defined, all technical and scientific terms used herein have the same meaning as commonly understood by one of ordinary skill in the art to which this invention pertains. The materials methods, and examples are illustrative only and not intended to be limiting. Suitable methods and materials are described below, although methods and materials similar or equivalent to those described herein can be used in the practice or testing of the present invention. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF THE DRAWINGS

FIG. 1 is the nucleotide and amino acid sequence (SEQ ID NO:3 and 4 respectively) of the tobacco small subunit (ss) Rubisco transit peptide and 5' portion of the mature ss Rubisco protein (underlined).

FIG. 4 is the nucleotide and amino acid sequence (SEQ ID NO:7 and 8, respectively) of an alfalfa cytosolic acetyl coA-carboxylase (ACCase) (GenBank Accession No. L25042 plus additional 3' untranslated sequences).

Like reference symbols in the various drawings indicate like elements.

DETAILED DESCRIPTION

Figure 2:
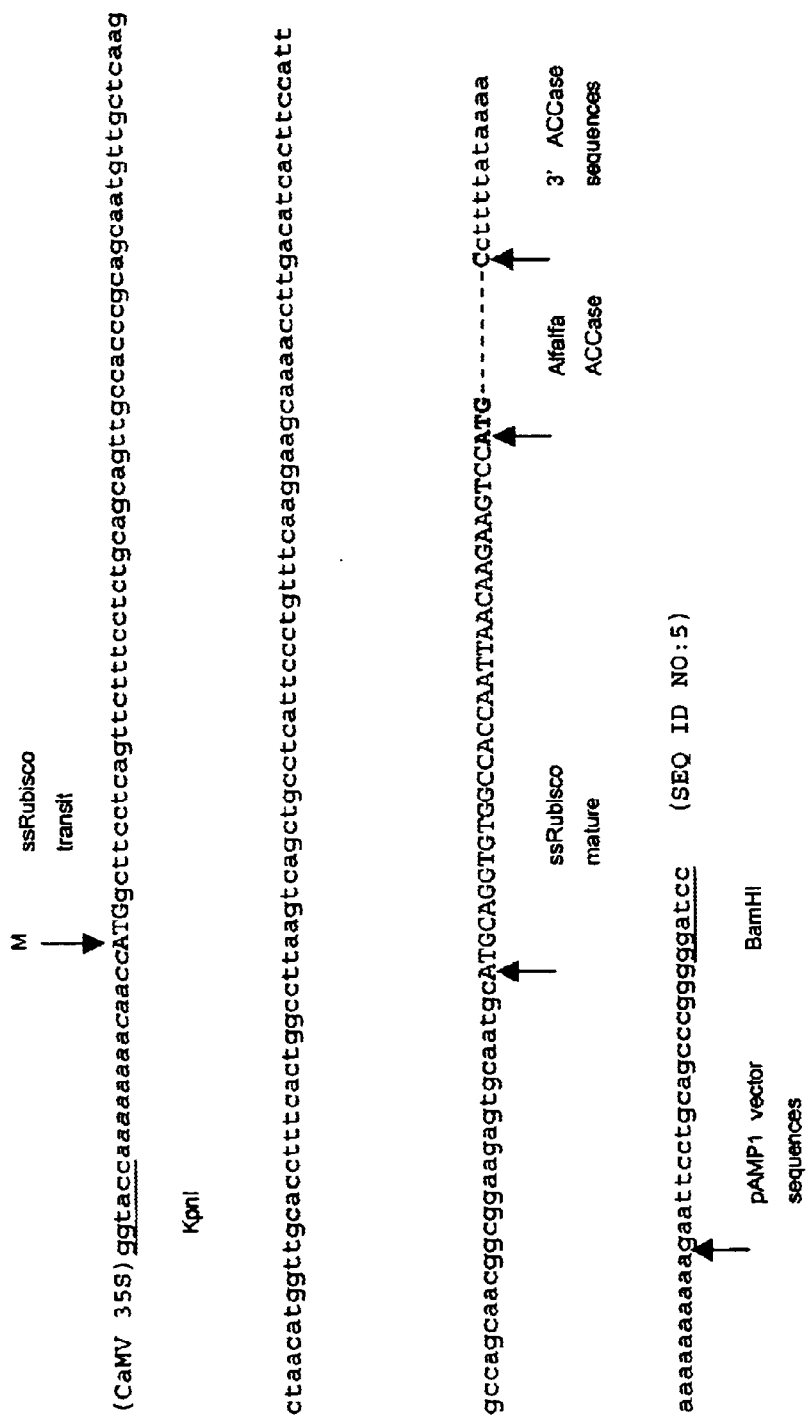
FIG. 2 is a representative +6ACCase construct (SEQ ID NO:5). The nucleotide sequence encoding a transit peptide and the 5' portion of a small subunit (ss) Rubisco gene from tobacco is shown operably linked to an alfalfa cytosolic ACCase coding sequence. A consensus sequence for initiation of translation is italicized and includes the 3' end of a 35S cauliflower mosaic virus (CaMV) promoter and the 5' sequence encoding the tobacco ssRubisco transit peptide. The ACCase sequence corresponds to a portion of the coding sequence and 3' untranslated sequences (See Genbank Accession No. L25042); for the entire ACCase coding sequence). Arrows indicate the methionine-initiated (M) start codon of the ssRubisco transit peptide, the beginning of the portion of the ssRubisco mature protein included in the construct, the beginning and end of the ACCase coding sequence as published in GenBank, and the end of the ACCase 3' untranslated sequences. The BamHI and KpnI restriction sites were used to clone the +6ACCase construct into the ptet vector.
Figure 3:
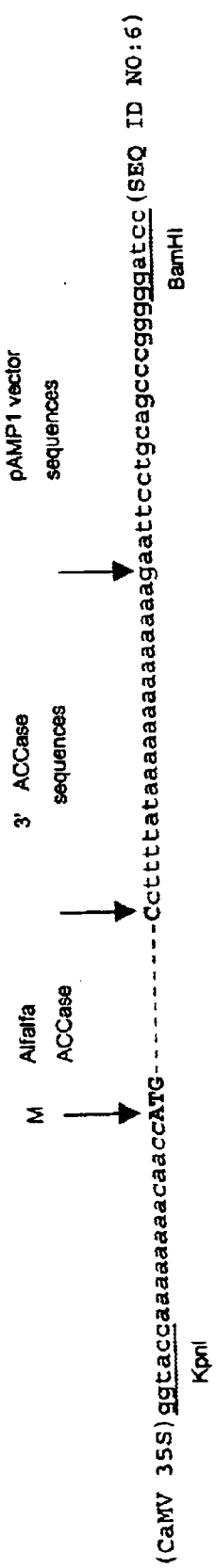
FIG. 3 is a representative −7ACCase construct (SEQ ID NO:6). The italicized consensus sequence for the initiation of translation includes the 3' end of a 35S cauliflower mosaic virus (CaMV) promoter and the 5' portion of an alfalfa cytosolic acetyl coA-carboxylase (ACCase) coding sequence (Shorrosh et al., 1994). The ACCase sequences are as described in the legend to FIG. 2. Arrows indicate the methionine-initiated (M) start codon, the end of the ACCase coding as published in GenBank and the end of the ACCase 3' untranslated sequences. The BamHI and KpnI restriction sites were used to clone the −7ACCase construct into the ptet vector.

All percent oil content and percent protein content are reported based upon dry weight. As used herein, "oil content" or "percent oil content" refers to the oil content in a particular tissue. "Oils" are typically triacylglycerols. Oil content can be measured in by NMR (using American Oil Chemists' Society (AOCS) Method AM 2-93 and AOCS Recommended Practice AK 4-95) or by NIR (using AOCS Method AK 3-94 and AOCS Procedure AM 1-92).

As used herein, "protein content" or "percent protein content" refers to the protein content in a particular tissue. The protein content in seeds typically includes storage proteins, as well as other peptide/polypeptide components. Protein content can be determined by NIR (using AOCS Method BA 4e-93).

As used herein, "high oleic acid" refers to an oleic acid ($C_{18:1}$) content in seeds greater than 70% based on total fatty acid composition after hydrolysis. A typical high oleic Brassica line exhibits an oleic acid content of at least 70%; for example, an oleic acid content of about 80%, or about 90% based on total fatty acid composition after hydrolysis. Oleic acid is typically measured by gas chromatography (GC) using AOCS Method Ce 1e-91.

As used herein, "high erucic acid" refers to an erucic acid ($C_{22:1}$) content greater than 45% based on total fatty acid composition after hydrolysis. A typical high erucic acid Brassica line would exhibit an erucic acid content of at least 45%; for example, an erucic acid content of 50%, 55% or even greater based on total fatty acid composition after hydrolysis. Erucic acid is typically measured by GC using AOCS Method Ce 1e-91.

As used herein, "FDA saturated fatty acid content" is the total of myristate ($C_{14:0}$), palmitate ($C_{16:0}$), stearate ($C_{18:0}$), arachidate ($C_{20:0}$), behenate ($C_{22:0}$) and lignocerate ($C_{24:0}$). Fatty acid profiles reported herein were obtained by GC (using AOCS Method Ce 1e-91).

As used herein, a "variety" is a group of plants that display little or no genetic variation between individuals for at least one trait. Varieties may be created by, e.g., several generations of self-pollination and selection, or vegetative propagation from a single parent using tissue or cell culture techniques.

As used herein, a "line" refers to a plant and its progeny produced from a single transformation.

Nucleic Acid Constructs

A nucleic acid construct useful in the invention comprises a multi-functional cytosolic acetyl coA-carboxylase (ACCase) coding sequence operably linked to a promoter. Suitable cytosolic ACCases include plant and animal cytosolic ACCases from organisms such as *Arabidopsis thaliana* (e.g., GenBank Accession No. L27074), *Brassica napus* (e.g., GenBank Accession No. X77576), *Zea mays* (e.g., GenBank Accession No. A25273) and *Homo sapiens* (e.g., GenBank Accession No. U19822). For example, a construct can contain a 35S cauliflower mosaic virus (CaMV) promoter and an alfalfa (i.e., *Medicago saliva*) cytosolic ACCase cDNA (e.g., GenBank Accession No. L25042).

Alternatively, a construct of the invention can contain ACCase nucleic acid sequences from *Saccharomyces cerivisiae* (e.g., GenBank Accession No. M92156), *Schizosaccharomyces pombe* (e.g., GenBank Accession No. D78169), *Ustilago maydis* (e.g., GenBank Accession No. Z46886), *Bos taurus* (bovine) (e.g., GenBank Accession No. AJ132890), *Rattus norvegicus* (rat) (e.g., GenBank Accession No. AB004329), *Ovis aries* (sheep) (e.g., GenBank Accession No. X80045), *Gallus gallus* (chicken) (e.g., GenBank Accession No. J03541), *Glycine max* (soybean) (e.g., GenBank Accession No. L42814), *Avena saliva* (oat) (e.g., GenBank Accession No. AF072737), *Triticum aestivum* (wheat) (e.g., GenBank Accession No. U39321) or *Phaseolus vulgaris* (bean) (e.g., GenBank Accession No. AF007803). A representative cloning strategy for producing a construct of the present invention is described herein. Other suitable methods for engineering constructs are described elsewhere, e.g., Sambrook et al., *Molecular Cloning: A Laboratory Manual*, 2nd ed., Cold Spring Harbor Laboratory Press (1989).

As used herein, "promoter" refers to nucleic acid sequences that, when operably linked to an ACCase coding sequence, direct transcription of the coding sequence such that it's gene product can be produced. Promoters can be described based on their activity (e.g., constitutive, inducible, tissue-specific or temporal-specific). Constitutive promoters are generally nucleic acid sequences that direct a relatively high level of transcription, and typically without great tissue- or temporal-specificity. Inducible promoters are typically nucleic acid sequences that regulate transcription in response to a stimulus (e.g. a physical or chemical stimulus). Tissue- or temporal-specific promoters are generally nucleic acid sequences that direct transcription that is biased toward a particular tissue or time (e.g., a particular developmental stage), respectively. Oftentimes, however, a promoter's activity does not fall under a single description.

Suitable promoters are known (e.g., Weising et al., *Ann Rev. Genetics* 22:421–478 (1988)). The following are representative promoters suitable for use in the invention described herein: regulatory sequences from fatty acid desaturase genes (e.g. Brassica fad2D or fad2F, see WO 00/07430); alcohol dehydrogenase promoter from corn; light inducible promoters such as the ribulose bisphosphate carboxylase (Rubisco) small subunit gene promoters from a variety of species; major chlorophyll a/b binding protein gene promoters; the 19S promoter of cauliflower mosaic virus (CaMV); a seed-specific promoter such as a napin or cruciferin seed-specific promoter; as well as synthetic or other natural promoters that are, for example, inducible, constitutive, tissue-specific or temporal-specific.

A nucleic acid construct optionally may contain a nucleic acid sequence encoding a transit peptide operably linked to an ACCase coding sequence. A transit peptide facilitates transport to plastids of the ACCase polypeptide to which the transit peptide is fired. Suitable transit peptides include any transit peptide encoded by a nuclear gene that directs transport of the encoded protein into the chloroplast.

A nucleic acid encoding a cytosolic ACCase may or may not contain introns within the coding sequence. Introns are nucleic acid sequences that are initially transcribed into RNA and subsequently removed. The number of introns in a transcript can vary, as can the size of each intron. Introns themselves possess very little conservation, but the splice site sequences (ie., the sequence at the exon-intron and intron-exon junctions) typically are highly conserved among eukaryotes. In addition, introns typically possess an internal conserved sequence corresponding to an branch site involved in intron removal. Nucleic acid sequences containing an ACCase open reading frame can be examined for introns using, for example, software such as the Sequence Analysis Software Package of the Genetics Computer Group (GCG) (University of Wisconsin Biotechnology Center, 1710 University Avenue, Madison, Wis. 53705). An ACCase nucleic acid having introns can be, for example, a genomic ACCase nucleic acid (e.g., GenBank Accession No. L27074). An ACCase nucleic acid lacking introns can be, for example, a complementary DNA (cDNA) of an ACCase mRNA nucleic acid (e.g., SEQ ID NO:7), or can be assembled (e.g., recombinantly) from individual exonic sequences.

It should be appreciated that many different nucleic acids will encode a polypeptide having a particular cytosolic ACCase amino acid sequence. The degeneracy of the genetic code is well known in the art, i.e., many amino acids are coded for by more than one nucleotide codon. It should also be appreciated that certain amino acid substitutions can be made within polypeptide sequences without affecting the function of the polypeptide. Conservative amino acid substitutions or substitutions of similar amino acids often are tolerated without affecting polypeptide function. Similar amino acids can be those that are similar in size and/or charge properties. Similarity between amino acids has been assessed in the art. For example, Dayhoff et al. (1978) in *Atlas of Protein Sequence and Structure*, Vol. 5, Suppl. 3, pp. 345–352, incorporated herein by reference, provides frequency tables for amino acid substitutions that can be employed as a measure of amino acid similarity.

Additional regulatory sequences may be useful in the nucleic acid constructs of the present invention, including, but not limited to, polyadenylation sequences, enhancers, introns, and the like. Such elements may not be necessary for expression of the ACCase coding sequence, although they may increase expression by affecting transcription, stability of the mRNA, translational efficiency, or the like. Such elements can be included in a nucleic acid construct as desired to obtain optimal expression of the ACCase nucleic acid in the host cell(s). Sufficient expression, however, may sometimes be obtained without such additional elements. A representative reference describing certain regulatory elements is Weising et al, *Ann Rev. Genetics* 22:421–478 (1988).

Transgenic Plants

In one aspect of the invention, transgenic plants are created by introducing an ACCase nucleic acid construct into a plant cell and growing the plant cell into a plant. Such plants contain and express the ACCase nucleic acid construct. Suitable techniques for introducing nucleic acids into plant cells to create such plants include, without limitation, Agrobacterium-mediated transformation, viral vector-mediated transformation, electroporation and particle gun transformation. Illustrative examples of transformation techniques are disclosed in U.S. Pat. No. 5,204,253, (describing biolistic trasformations), U.S. Pat. No. 6,051,756 (describing biolistic transformation of Brassica) and U.S. Pat. No. 5,188,958 (describing Agrobacterium transformation). Transformation methods utilizing the Ti and Ri plasmids of Agrobacterium spp. typically use binary-type vectors (e.g., ptet1, pBin19) (Walkerpeach et al., in *Plant Molecular Biology Manual*, Gelvin & Schilperoort, eds., Kluwer Dordrecht, C1:1–19 (1994)).

Techniques are known for the introduction of DNA into dicots as well as monocots, as are the techniques for culturing such tissues and regenerating plants. If cell or tissue cultures are used as the recipient tissue for transformation, plants can be regenerated from transformed cultures by techniques known to those skilled in the art. Suitable dicots include plants such as alfalfa, soybean, rapeseed (high erucic and canola), and sunflower. Monocots that have been successfully transformed and regenerated in the art include wheat, corn, rye, rice, sorghum and asparagus (see, e.g., U.S. Pat. Nos. 5,484,956 and 5,550,318).

Preferred species for generating transgenic plants of the present invention include, without limitation, oil-producing species, such as soybean (*Glycine max*), rapeseed (e.g., *Brassica napus*, *B. rapa* and *B. juncea*) (both Spring and Winter maturing types within each species), sunflower (*Helianthus annus*), castor bean (*Ricinus communis*), safflower (*Carthamus tinctorius*), palm (e.g., *Elaeis guineensis*), coconut (e.g., *Cocos nucifera*), meadowfoam (e.g., *Limnanthes alba alba* and *L. douglasii*), cottonseed (e.g. *Gossypium hirsutum*), olive (e.g., *Olea europaea*), peanut (e.g., *Arachis hypogaea*), flax (e.g., *Linum usitatissimum*), sesame (e.g., *Sesamum indicum*) and crambe (e.g., *Crambe abyssinica* or *C. hispanica*). Accordingly, suitable families include, but are not limited to, Solanaceae, Leguminaceae, Brassicaceae and Asteraccae. A transgenic plant of the invention typically is a member of a plant variety within the families or species mentioned above.

As used herein, a transgenic plant also refers to progeny of an initial transgenic plant. Progeny includes descendants of a particular plant or plant variety, e.g., seeds developed on a particular plant. Progeny of a plant also includes seeds formed on $F_1$, $F_2$, $F_3$, and subsequent generation plants, or seeds formed on $BC_1$, $BC_2$, BC3, and subsequent generation plants. Seeds produced by a transgenic plant can be grown and then selfed (or out-crossed and selfed) to obtain plants homozygous for the construct. Seeds can be analyzed to identify those homozygotes having the desired level of expression of a construct. Alternatively, transgenic plants and progeny thereof may be obtained by vegetative propagation of a transformed plant cell (for those species amenable to such techniques).

Transgenic plants can be used in commercial breeding programs for the species of interest or can be crossed or bred to plants of related crop species. Phenotypes conferred by expression of an ACCase nucleic acid construct can be transferred from one species to another species by, for example, protoplast fusion. Such breeding programs are useful to incorporate other agronomic or specialty traits of interest, e.g., herbicide tolerance or a high oleic acid content in seeds.

Methods

In one aspect of the invention, there are provided methods of generating a plant that produces seeds exhibiting a statistically significant increase in oil content. The method includes introducing a nucleic acid construct containing B promoter and an ACCase coding sequence into a plant and selecting progeny that produce seeds with increased oil content as compared to seeds from a corresponding plant lacking the ACCase nucleic acid construct, e.g., seeds from a plant having the same or similar genetic background as the transgenic plant but which does not have the cytosolic ACCase construct. Such progeny are identified after one or more generations of selection, e.g., one generation, three or more generations, or six or more generations. By way of example, selection may be carried out initially, e.g., the first and second generations, by selecting those progeny possessing the ACCase construct, and selection in subsequent generations may be carried out by identifying those progeny that possess the ACCase construct as well as elevated seed oil content.

Also provided by the invention are methods of producing seeds with a statistically significant increase in oil content. The methods include introducing a nucleic acid construct containing a promoter and an ACCase coding sequence into one or more plant cells and regenerating such plant cells into one or more plants. Seeds exhibiting statistically significantly increased oil content can then be harvested from selected progeny of the plant.

Further provided by the invention are methods of increasing the oil content in seeds. The methods include introducing a nucleic acid construct containing a promoter and a cytosolic ACCase coding sequence into a plant and selecting progeny after at least one generation of selection that produce seed with increased oil content as compared to corresponding seeds produced from plants lacking the recombinant ACCase nucleic acid.

The following Table provides relative percent oil and protein content on a dry weight basis (unless indicated otherwise) in several plants, particularly oilseed plants, that can be used in the present invention.

| Plant | % Oil | % Protein | Key |
|---|---|---|---|
| Soybean (*Glycine max*) | ~20 | ~40 | c |
| Rapeseed (*Brassica napus*) | 40–44 | 38–41 (oil free meal) | c; d |
| Sunflower (*Helianthus annus*) | 40 | | d |
| Castor bean (*Ricinus communis*) | 50 | | a |
| Safflower (*Carthamus tinctorius*) | 36.8–47.7 | 15.4–22.5 | d |
| Crambe (*Crambe abyssinica*) | 30–35 | ~28 | b |
| Palm (*Elaeis guineensis*) | 20 | | c; per fresh fruit bunch (~20% moisture); dried kernels |
| | >50 | | |
| Coconut (*Cocos nucifera*) | 34 | 3.5 | d; coconut flesh (50% moisture); dried kernels |
| | 69 | | |
| Maize (*Zea mays*) | 3.1–5.7 | 6–12 | c; d |
| Cottonseed (*Gossypium hirsutum*) | 25–30 | 25–30 | d; kernel |
| Olive (*Olea europaea*) | 19.6 | 1.6 | fruit (52.4% moisture) |
| Peanut (*Arachis hypogaea*) | 36–56 | 25–30 | c; (unknown moisture) |
| Flax (*Linum usitatissimum*) | 35–45 | | d; per fruit capsule (~10 seeds/fruit) |
| Sesame (*Sesamum indicum*) | 53.3–57.5 | 25–30 | d; (5–7% moisture) | a Brigham RD, 1993, Castor: Return of an old crop, p 380–3. In New Crops, Janick, J & Simon, J E, eds. Wiley, N Y.
b Grombacher et al., Cooperative Extension, Institute of Agriculture and Natural Resources, University of Nebraska-Lincoln, Crambe production, Publication G93-1126A, G1126 (Field Crops), F-17 (Misc. Crops); see also pubs@unlvm.unl.edu
c In Principles of Cultivar Development, 1987, Fehr, W R, ed., Macmillan Publishing Co., N Y.
d In 5$^{th}$ Edition Bailey's Industrial Oil & Fat Products, Vol. 2, Edible Oil & Fat Products: Oils and Oil Seeds, 1996, Hui, Y H, ed., Wiley, N Y.

The present invention describes a novel method of making plants that produce seeds with a statistically significant increase in oil content. As used herein, "statistically significant" refers to a p-value of less than 0.05, e.g., a p-value of less than 0.025 or a p-value of less than 0.01, using an appropriate measure of statistical significance, e.g., a one-tailed two sample t-test.

Plants of the invention produce seeds that exhibit an increase in oil content that is statistically significant relative to seeds produced by plants that lack a cytosolic ACCase construct. Plants produced by the method of the present invention produce seeds having an increase in oil of from about 5% to about 25% over the oil content in seeds produced by untransformed control plants. For example, the increase in oil content for plants described herein is from about 5% to about 20%, or from about 5% to about 15%, or from about 10% to about 20%, relative to plants that lack a cytosolic ACCase construct.

The seeds of several different Brassica napus lines from a −7ACCase/Westar transformation have been deposited with the American Type Culture Collection (ATCC), 10801 University Blvd., Manassas, Va., 20110-2209, and have the following accession numbers.

| Line | Accession No. | Deposit Date |
|---|---|---|
| Tao-001-30-02 | | |
| Tao-001-31-02 | | |
| Tao-001-56-01 | | |

-continued

| Line | Accession No. | Deposit Date |
| --- | --- | --- |
| Tao-001-56-06 | | |
| Tao-001-65-08 | | |

Seeds and plants of plant varieties made from the transgenic plants described herein are included within the scope of the invention, as well as progeny of these varieties that possess the novel characteristics recited herein. Oil extracted from such varieties or from similar varieties is also within the scope of the invention.

Nucleic acid constructs, plants and methods described herein provide for more efficient production of oil for food and industrial applications (e.g., engine lubricants, hydraulic fluids, etc.). For example, plants described herein produce a greater yield of oil per acre planted compared to plants lacking a cytosolic ACCase construct. In addition, there is increased oil yield during the processing of such seeds.

The invention will be further described in the following examples, which do not limit the scope of the invention described in the claims.

EXAMPLES

Example 1

Constructs

The pSP72 vector (Promega) was digested with XhoI and SalI and subsequently religated to remove the PvuII site. This modified vector was designated ModpSP72. The tobacco small subunit Rubisco (ssRubisco, also known as ribulose 1,5-bisphosphate carboxylase) transit peptide was amplified by PCR from a tobacco ssRubisco gene/pet11d template using a 5' primer (5'-CAUCAUCAUCAUAUC GATAGGTACCAAAAAAA CAACCATGGCTTCCTCA GTTCTR) (SEQ ID NO:1) and a 3' primer (5'-CUACUAC UACUAGCTAGCCATGGACTTCTTGTTAATTGGTGG CCA) (SEQ ID NO:2). The 5' primer was designed to contain ClaI, KpnI, and NcoI sites, and the 3' primer was engineered to contain NcoI and NheI sites. The amplified transit peptide DNA was annealed into the pAMP1 vector (Gibco BRL) and both strands were sequenced to confirm fidelity. This construct was designated +Transit/pAMP1. To generate a construct lacking the transit peptide (−Transit/pAMP), +Transit/pAMP1 was digested with NcoI and religated.

The cloning of a fragment designated 209/180 from an alfalfa cytosolic acetyl coA-carboxylase (ACCase) into the pAMP1 vector to produce 209/180/pAMP1 is described in Shorrosh et al. (1994, Proc. Natl. Acad. Sci. USA, 91:4323–27). A fragment designated 147/136 was PCR amplified using primers 147 and 136 (Shorrosh et al., 1994), which was subsequently subcloned into the pAMP1 vector to generate a 147/136/pAMP1 construct The 209/180 fragment was removed from the pAMP1 vector by digesting with KpnI and BamHI and subcloned into the KpnI/BamHI sites of ModpSP72 to generate a 209/180/pSP72 construct. The 147/136/pAMP1 construct was digested with SnaBI and BamHI and the insert containing the 147/136 fragment was subcloned into the SnaBI/BamHI sites of the 209/180/pSP72 construct to generate a 209/136/pSP72 construct.

Clone "T1", corresponding to a partial alfalfa ACCase cDNA and described in Shorrosh et al., 1994, was digested with PvuII and BamHI and subcloned into the 209/136/pSP72 construct at the PvuII/BamHI sites to generate 209-T/pSP72. Additionally, a clone designated 3X, corresponding to a partial alfalfa ACCase cDNA (essentially the M2 fragment as described in Shorrosh et al., 1994, with additional 5' and 3' flanking sequences to facilitate cloning), was digested with EcoR47III and BamHI and subcloned into the 209-T/pSP72 construct at the EcoR47III/BamHI sites to generate 209-3X/pSP72. This construct contains a full-length alfalfa cytosolic ACCase cDNA coding sequence in the pSP72 vector.

The 209-3X/pSP72 construct was digested with KpnI and BamHI and subcloned into the +Transit/pAMPI construct at the KpnI/BamHI sites to generate a construct designated +6ACCase/pAMP1. +6ACCase/pAMP1 contains a full-length alfalfa ACCase cDNA with a transit peptide at the 5' end in the same reading frame as the ACCase coding sequence. The +6ACCase/pAMP1 construct was then digested with NheI and BamHI and the full-length alfalfa ACCase cDNA, including the transit peptide, was subcloned into the Agrobacterium binary vector, ptet1 (provided by Dr. C. Gatz, Institute fur Genbiologische, Berlin), at the NheI/BamHI sites adjacent to the cauliflower mosaic virus (CaMV) 35S promoter. This manipulation generated +6ACCase/ptet1. Similarly, the 209-3X/pSP72 construct was digested with NheI/BamHI and the full-length alfalfa ACCase cDNA was subcloned into the −Transit/pAMP1 construct at the NheI/BamHI sites to generate −7ACCase/pAMP1. The −7ACCase/pAMP1 construct was then digested with KpnI and BamHI and the full-length alfalfa ACCase cDNA was subcloned into the ptet1 binary vector at the KpnI/BamHI sites adjacent to the CaMV 35S promoter to produce −7ACCase/ptet1. The −7ACCase/ptet1 construct contains a full-length alfalfa ACCase cDNA but lacks a transit peptide.

Example 2

Transgenic Plants

The +6ACCase/ptet1 and −7ACCase/ptet1 constructs of Example 1 were used to transform Agrobacterium LBA4404. The resulting Agrobacterium transformants were each co-cultivated separately with B. napus hypocotyls and cultured consecutively on incubation, selection (containing kanamycin) and regeneration media until green shoots were produced. Regenerated plantlets were transferred to the greenhouse and grown to maturity. Each T1 plant (N=240) was selfed and the resulting T2 seeds were harvested from each individual T1 plant.

The ACCase constructs were introduced into B. napus hypocotyls of three different canola varieties as follows. A construct designated −7ACCase was introduced into Westar, a canola variety registered in Canada; and a construct designated +6ACCase was introduced into Oscar, a canola variety registered in Australia (App. No. 19921009, Jun. 19, 1996) or IMC 03, a Cargill proprietary low linolenic acid canola variety. Table 1 shows a typical fatty acid profile for each of the Brassica varieties used in the transformations.

TABLE 1

Typical fatty acid profile of Westar, Oscar and IMC 03 seeds

| Fatty acid | Westar | Oscar | IMC 03 |
| --- | --- | --- | --- |
| $C_{16:0}$ | 3.7[1] | 3.7 | 3.9 |
| $C_{16:1}$ | 0.1 | 0.1 | 0.1 |

TABLE 1-continued

Typical fatty acid profile of Westar, Oscar and IMC 03 seeds

| Fatty acid | Westar | Oscar | IMC 03 |
|---|---|---|---|
| $C_{18:0}$ | 2.5 | 2.5 | 1.95 |
| $C_{18:1}$ | 65.0 | 60 | 65.6 |
| $C_{18:2}$ | 17.6 | 22.0 | 18.0 |
| $C_{18:3}$ | 8.0 | 10.0 | 3.00 |
| $C_{20:0}$ | 0.5 | 0.5 | 0.5 |
| $C_{20:1}$ | 1.3 | 1.3 | 1.5 |
| $C_{20:2}$ | 0.1 | 0.1 | 0.1 |
| $C_{22:0}$ | 0.1 | 0.1 | 0.1 |
| $C_{22:1}$ | 0.1 | 0.1 | 0.05 |
| $C_{24:0}$ | 0.1 | 0.1 | 0.1 |
| $C_{24:1}$ | 0.1 | 0.1 | 0.1 |
| FDA | 6.9 | 6.9 | 6.55 |
| % Oil | 45.0 | 41.0 | 46.0 |
| % Protein | 26.97[2,3] | — | 22.46[3] |

[1]percent;
[2]from Principles in Cultivar Development, Vol. 2, Crop Species, W. R. Fehr, ed., pp. 443;
[3]percent protein content was estimated based upon the percent protein content reported for the air-dried, oil-free seed meal using the oil content reported and assuming a 5% moisture content;
— Unknown.

Example 3

Preparation of Fatty Acid Methyl Esters and Fatty Acid Analysis of Seed by Capillary Gas Liquid Chromatography (GLC)

The following describes a means for quantifying fatty acid composition in canola seed. To prepare samples, approximately 150 mg of seed is placed into a 15 ml polypropylene centrifuge tube. The seed is broken apart and 0.6 ml of methanolic KOH solution is added to the tube. After mixing on a vortex mixer for approximately 30 sec, the tube is placed in a water bath at 60° C. for 60 sec. About 4.0 ml of saturated NaCl solution is added to the tube followed by 1.0 ml of iso-octane and the sample mixed on a vortex mixer for an additional 30 sec. The sample is centrifuged for 5 min to separate and purify the organic layer. Approximately 700 μl of the organic layer, which contains the fatty acid methyl esters, is removed from the tube and placed into a GC autosampler vial. The vial is purged with nitrogen gas to remove the oxygen and preserve the sample.

Samples are analyzed, based on AOCS Method Ce 1e-91, by injecting 1.0 μl into a Hewlett Packard 6890 gas chromatograph by means of an autosampler. A normalized percentage is calculated and reported for each fatty acid in the sample. The GC conditions are as follows:

Column: 5 m×0.32 mm DB-Wax (0.5 μm film thickness);

Detector: FID;

Inlet temp.: 250° C.;

Detector temp.: 250° C.;

Split ratio: 100:1;

Carrier gas: helium at 30.0 ml/min; and

Oven program: 1.0 min at 220° C.; 10° C./min up to 245° C.; and 3.0 min at 245° C.

Example 4

Determination of Oil and Moisture Content in Canola Seed by NMR Spectroscopy

The following is a non-destructive method for determining oil and moisture content in samples of canola seed by means of nuclear magnetic resonance spectroscopy. An Oxford MQA6005 NMR Analyzer (Oxford Analytical Instruments Limited, Concord, Mass.) is calibrated according to manufacturer specifications. Six samples of canola seed (~22 g/sample) are used for calibration. Samples are selected to represent the oil and moisture ranges over which most unknown samples are expected to fall. The oil content of each sample is determined by Soxhlet extraction (based on AOCS Method Am 2-93). Moisture content is determined by gravimetric means (based on AOCS Method Ai 2-75). The response of each sample is then measured on the NMR instrument. Two calibration curves (one for oil and one for moisture) are prepared using the data collected.

Samples containing unknown amounts of oil and moisture are analyzed according to the instrument manufacturer instructions (based on AOCS Recommended Practice Ak 4-95). The response of each sample is collected and stored by a computer. The results are calculated and expressed as "Oil %", "Moisture %", and "Oil % Normalized to Dry Mass" (conversion from Oil % (as is) to Oil % on a dry basis is calculated using the following formula: Oil % (dry)=Oil % (as is)/[1-(Moisture %100)]).

Example 5

Determination of Percent Oil, Moisture, Protein, Chlorophyll, and Fatty Acids by NIR Spectroscope The following method provides a means of predicting the levels of oil, moisture, protein, chlorophyll, oleic acid ($C_{18:0}$), linoleic acid ($C_{18:1}$), and linolenic acid ($C_{18:2}$) in canola seed samples by means of near infra-red reflectance spectroscopy.

A Foss NIR Systems model 6500 Feed and Forage Analyzer (Foss North America, Eden Prairie, Minn.) is calibrated according to the manufacturer's recommendations. Canola seed samples, which represented wide ranges of the sample constituents listed above, are collected for calibration. Lab analysis results are determined using accepted methodology (ie., oil, AOCS Method Ak 3-94; moisture, AOCS Method Ai 2-75; fatty acid, AOCS Method CE 1e-91 and AOCS Method CE 2-66; chlorophyll, AOCS Method CC 13D-55; protein, AOCS Method BA 4e-93; and glucosinolates, AOCS Method Ak 1-92). Instrument response is also measured for each sample. A calibration equation is calculated for each constituent by means of chemometrics. These equations are combined into one computer file and are used for prediction of the constituents contained in unknown canola samples.

Seed samples containing unknown levels of the above constituents are prepared by removing foreign material from the sample. Cleaned whole seed is placed into the instrument sample cell and the cell is placed into the instrument sample assembly. Analysis is carried out according to instrument manufacturer instructions (based on AOCS Procedure Am 1-92). The results are predicted and reported as % constituent (% oil and protein are reported based on dry weight). Conversion from 'dry weight' basis to 'as is' basis for oil and protein is calculated using the following formula:

constituent (as is)=constituent (dry wt.)×[1-(% moisture/100)].

Example 6

T1 Plants and T2 Seeds

A total of 126-7ACCase/Westar plants were regenerated in a greenhouse from the plantlets described in Example 2.

Each T1 plant was selfed and a sample of T2 seeds from each plant was analyzed for fatty acid composition by gas chromatography as described in Example 3. T2 seeds had fatty acid compositions that were not significantly different from the fatty acid profile of the Westar background variety.

Table 2 shows the mean fatty acid profile (±standard deviation) for the −7ACCase/Westar transformation. 12 seeds from each T1 plant were advanced (i.e., no selection was performed on 72 seeds) such that 5–10 seeds from each T1 plant were grown individually in a single row in the greenhouse.

TABLE 2

Mean fatty acid profile of T2 seeds

| Fatty acid | −7ACCase/Westar |
|---|---|
| $C_{14:0}$ | 0.07 (0.04)[1] |
| $C_{16:0}$ | 4.59 (0.69) |
| $C_{16:1}$ | 0.31 (0.13) |
| $C_{18:0}$ | 2.28 (0.45) |
| $C_{18:1}$ | 61.61 (3.53) |
| $C_{18:2}$ | 20.18 (2.27) |
| $C_{18:3}$ | 7.95 (1.04) |
| $C_{20:0}$ | 0.77 (0.12) |
| $C_{20:1}$ | 1.23 (0.10) |
| $C_{20:2}$ | 0.08 (0.02) |
| $C_{22:0}$ | 0.45 (0.09) |
| $C_{22:1}$ | 0.03 (0.03) |
| $C_{24:0}$ | 0.24 (0.10) |
| $C_{24:1}$ | 0.24 (0.17) |
| FDA | 8.39 (1.22) |

[1]mean in percent (± standard deviation)

Table 3 shows fatty acid profiles of T2 seeds from representative individual lines from the −7ACCase/Westar transformation.

TABLE 3

Fatty acid profile of T2 seeds from representative individual −7ACCase/Westar Brassica lines

| | 001-01[1] | 001-120 | 001-121 | 001-31 |
|---|---|---|---|---|
| $C_{14:0}$ | 0.103[2] | 0.448 | 0.154 | 0.056 |
| $C_{16:0}$ | 7.720 | 7.053 | 6.339 | 4.222 |
| $C_{16:1}$ | 0.776 | 0.821 | 0.820 | 0.249 |
| $C_{18:0}$ | 3.181 | 3.107 | 4.213 | 1.988 |
| $C_{18:1}$ | 55.584 | 51.827 | 50.624 | 64.292 |
| $C_{18:2}$ | 22.659 | 24.794 | 25.949 | 18.319 |
| $C_{18:3}$ | 6.806 | 8.343 | 7.041 | 8.106 |
| $C_{20:0}$ | 1.170 | 0.969 | 1.235 | 0.688 |
| $C_{20:1}$ | 0.950 | 0.815 | 0.902 | 1.337 |
| $C_{20:2}$ | 0.000 | 0.065 | 0.082 | 0.065 |
| $C_{22:0}$ | 1.170 | 0.578 | 0.912 | 0.381 |
| $C_{22:1}$ | 0.000 | 0.024 | 0.188 | 0.000 |
| $C_{24:0}$ | 0.379 | 0.421 | 0.574 | 0.168 |
| $C_{24:1}$ | 0.000 | 0.735 | 0.966 | 0.129 |
| FDA | 13.225 | 12.576 | 13.427 | 7.504 |

[1]line designation;
[2]%

Example 7

T2 Plants and T3 Seeds

A total of 834 T2 plants from 126 lines were selfed and the resulting T3 seed analyzed for fatty acid composition by gas chromatography as described in Example 3.

Table 4 shows summary statistics (mean±standard deviation) of fatty acid profiles of seeds from the total population of T3 plants produced in the −7ACCase/Westar transformation, from those T3 plants selected for advancement and from plants corresponding to the non-transgenic Westar variety. Data for the non-transgenic control plants was obtained from 19 Westar plants grown under similar conditions.

TABLE 4

Mean fatty acid profile of T3 seeds

| | −7ACCase/Westar | | |
|---|---|---|---|
| Fatty acid | Total[1] | Sel[1] | Control[1] |
| $C_{14:0}$ | 0.06[2] | 0.06 | 0.06 |
| | (0.02) | (0.03) | (0.02) |
| $C_{16:0}$ | 4.71 | 4.90 | 4.45 |
| | (0.79) | (1.03) | (0.51) |
| $C_{16:1}$ | 0.27 | 0.28 | 0.23 |
| | (0.10) | (0.13) | (0.10) |
| $C_{18:0}$ | 2.84 | 3.25 | 2.68 |
| | (0.68) | (0.68) | (0.52) |
| $C_{18:1}$ | 66.62 | 67.20 | 69.76 |
| | (5.34) | (6.69) | (3.41) |
| $C_{18:2}$ | 15.67 | 14.46 | 13.78 |
| | (3.50) | (3.88) | (2.46) |
| $C_{18:3}$ | 5.68 | 5.20 | 4.90 |
| | (1.43) | (1.26) | (1.05) |
| $C_{20:0}$ | 1.14 | 1.32 | 1.08 |
| | (0.26) | (0.21) | (0.29) |
| $C_{20:1}$ | 1.38 | 1.43 | 1.41 |
| | (0.21) | (0.24) | (0.14) |
| $C_{20:2}$ | 0.07 | 0.06 | 0.05 |
| | (0.02) | (0.02) | (0.02) |
| $C_{22:0}$ | 0.74 | 0.87 | 0.75 |
| | (0.22) | (0.21) | (0.16) |
| $C_{22:1}$ | 0.03 | 0.03 | 0.02 |
| | (0.04) | (0.04) | (0.02) |
| $C_{24:0}$ | 0.50 | 0.60 | 0.55 |
| | (0.16) | (0.13) | (0.15) |
| $C_{24:1}$ | 0.31 | 0.34 | 0.28 |
| | (0.13) | (0.13) | (0.06) |
| FDA | 9.99 | 11.00 | 9.56 |
| | (1.72) | (1.84) | (1.09) |

[1]Total, mean composition of all T2 plants; Sel, mean composition of T2 plants selected for advancement; Control, mean composition of non-transformed Westar plants;
[2]mean in percent (± standard deviation).

Three hundred ninety-five plots of T2 plants (representing 104 lines) from the −7ACCase/Westar transformation were selected for advancement based on T3 seeds exhibiting one or more of the following properties in fatty acid composition: $C_{18:0} > 3.45\%$, $C_{18:2} < 13.1\%$, $C_{18:3} < 4.51\%$, $C_{20:0} > 1.55\%$, or FDA saturates (defined as the sum of $C_{14:0}$, $C_{16:0}$, $C_{18:0}$, $C_{20:0}$, $C_{22:0}$ and $C_{24:0}$) > 10.5%.

Table 5 shows the fatty acid profile of T3 seed from representative individual lines from the −7ACCase/Westar transformation that were selected for advancement. Bolded numbers indicate criteria used to select and advance the plants.

TABLE 5

Fatty acid profile of T3 seeds from representative −7ACCase/Westar lines selected for advancement

| Fatty acid | 001-26-01[1] | 001-27-12 | 001-30-02 | 001-31-05 | 001-31-07 | 001-78-04 |
|---|---|---|---|---|---|---|
| $C_{14:0}$ | 0.0755[2] | 0.1100 | 0.0371 | 0.0393 | 0.0481 | 0.1419 |
| $C_{16:0}$ | 7.3213 | 10.6772 | 3.9496 | 3.8797 | 4.1826 | 10.7381 |
| $C_{16:1}$ | 0.3434 | 0.6230 | 0.1360 | 0.1408 | 0.2025 | 0.6661 |
| $C_{18:0}$ | 4.1630 | 2.9979 | 2.1986 | 2.6323 | 3.0341 | 7.5048 |
| $C_{18:1}$ | 42.6632 | 28.1662 | 72.7333 | 72.5224 | 70.0784 | 31.4668 |
| $C_{18:2}$ | 29.2415 | 37.0096 | 11.5253 | 11.4008 | 12.2550 | 29.4236 |

TABLE 5-continued

Fatty acid profile of T3 seeds from representative -7ACCase/Westar lines selected for advancement

| Fatty acid | 001-26-01[1] | 001-27-12 | 001-30-02 | 001-31-05 | 001-31-07 | 001-78-04 |
|---|---|---|---|---|---|---|
| $C_{18:3}$ | 9.5494 | 12.4735 | 4.5227 | 4.6344 | 5.1038 | 10.4718 |
| $C_{20:0}$ | 1.7108 | 1.5811 | 1.1132 | 1.2070 | 1.3821 | 2.6041 |
| $C_{20:1}$ | 2.2521 | 2.4504 | 1.7807 | 1.6792 | 1.6406 | 2.6668 |
| $C_{20:2}$ | 0.1620 | 0.1600 | 0.0726 | 0.0724 | 0.0700 | 0.1295 |
| $C_{22:0}$ | 1.1188 | 1.7861 | 0.9534 | 0.9449 | 0.9628 | 1.8995 |
| $C_{22:1}$ | 0.1219 | 0.2030 | 0.1075 | 0.0875 | 0.0000 | 0.0000 |
| $C_{24:0}$ | 0.7574 | 0.9286 | 0.5629 | 0.5129 | 0.6498 | 1.6442 |
| $C_{24:1}$ | 0.5197 | 0.8334 | 0.3071 | 0.2465 | 0.3903 | 0.6428 |
| FDA | 15.1468 | 18.0809 | 8.8148 | 9.2161 | 10.2594 | 24.5325 |

[1]line designation;
[2]%

Example 8

T3 Plants and T4 Seeds

About 0.5 g of T3 seed from each T2 plant selected for advancement as described in Example 7, were planted in field plots in Colorado, USA. T4 seeds were collected and combined from 20 random T3 plants from each line and analyzed for fatty acid composition (by GC; see Example 3) and oil content (by NMR; see Example 4). Following random bulk T4 seed analysis from each plot, 5–10 T4 seeds from those lines exhibiting increased oil content were advanced individually in the greenhouse.

Thirteen T3 lines with oil content of 48.7% to 50%/ were advanced and one T3 line with oil content of 48.1% was advanced from the −7ACCase/Westar transformation. Table 6 shows summary statistics (mean±standard deviation) for seed fatty acid profiles of the total T4 population, the plants selected for advancement and corresponding non-transgenic control plants. Data for the non-transgenic control population was obtained from 139 Westar plants transgenic for an fae1 gene. The fae1 gene elongates $C_{18:1}$ to $C_{20:1}$, thereby resulting in an accumulation of $C_{20:1}$ in plants transgenic for fae1, but does not affect oil content.

TABLE 6

Mean fatty acid profile and oil content of T4 seeds

| | -7ACCase/Westar | | |
|---|---|---|---|
| Fatty acid | Total[1] | Sel[1] | Control[1] |
| $C_{14:0}$ | 0.06[2] | 0.06 | 0.07 |
| | (0.01) | (0.01) | (0.03) |
| $C_{16:0}$ | 3.52 | 3.52 | 3.48 |
| | (0.40) | (0.12) | (0.52) |
| $C_{16:1}$ | 0.19 | 0.18 | 0.19 |
| | (0.03) | (0.01) | (0.05) |
| $C_{18:0}$ | 3.00 | 2.12 | 2.15 |
| | (8.76) | (0.13) | (0.24) |
| $C_{18:1}$ | 68.58 | 69.83 | 64.60 |
| | (6.64) | (0.33) | (8.61) |
| $C_{18:2}$ | 15.26 | 15.30 | 14.68 |
| | (1.98) | (0.44) | (1.32) |
| $C_{18:3}$ | 6.42 | 6.40 | 6.49 |
| | (0.90) | (0.29) | (0.58) |
| $C_{20:0}$ | 0.71 | 0.66 | 0.75 |
| | (0.11) | (0.01) | (0.18) |
| $C_{20:1}$ | 1.26 | 1.18 | 5.47 |
| | (0.19) | (0.05) | (7.83) |
| $C_{20:2}$ | 0.05 | 0.05 | 0.14 |
| | (0.01) | (0.00) | (0.18) |

TABLE 6-continued

Mean fatty acid profile and oil content of T4 seeds

| | -7ACCase/Westar | | |
|---|---|---|---|
| Fatty acid | Total[1] | Sel[1] | Control[1] |
| $C_{22:0}$ | 0.34 | 0.29 | 0.32 |
| | (0.04) | (0.01) | (0.04) |
| $C_{22:1}$ | 0.08 | 0.05 | 0.92 |
| | (0.44) | (0.08) | (2.23) |
| $C_{24:0}$ | 0.30 | 0.22 | 0.22 |
| | (0.29) | (0.04) | (0.09) |
| $C_{24:1}$ | 0.24 | 0.15 | 0.52 |
| | (0.25) | (0.09) | (0.57) |
| FDA | 7.92 | 6.86 | 6.98 |
| | (8.58) | (0.16) | (0.65) |
| % Oil | 45.7 | 49.1 | 45.5 |
| | (3.2) | (0.51) | (1.92) |

[1]Total, mean composition of all T3 plants; Sel, mean composition of T3 plants selected for advancement; Control, mean composition of non-transformed Westar plants;
[2]mean in percent (± standard deviation).

Table 7 shows the fatty acid profiles of T4 seed from representative individual lines from the −7ACCase/Westar transformation that were selected for advancement.

TABLE 7

Fatty acid profile and oil content of T4 seeds from representative -7ACCase/Westar lines selected for advancement

| Fatty acid | 001-31-07[1] | 001-30-02 | 001-31-06 | 001-30-05 |
|---|---|---|---|---|
| $C_{14:0}$ | 0.06[2] | 0.06 | 0.06 | 0.07 |
| $C_{16:0}$ | 3.59 | 3.52 | 3.42 | 3.70 |
| $C_{16:1}$ | 0.19 | 0.17 | 0.17 | 0.18 |
| $C_{18:0}$ | 2.01 | 2.10 | 2.07 | 2.10 |
| $C_{18:1}$ | 69.76 | 69.47 | 70.12 | 69.49 |
| $C_{18:2}$ | 15.64 | 16.21 | 15.08 | 15.49 |
| $C_{18:3}$ | 6.24 | 5.99 | 6.48 | 6.45 |
| $C_{20:0}$ | 0.65 | 0.65 | 0.66 | 0.67 |
| $C_{20:1}$ | 1.13 | 1.14 | 1.18 | 1.15 |
| $C_{20:2}$ | 0.04 | 0.05 | 0.05 | 0.05 |
| $C_{22:0}$ | 0.30 | 0.28 | 0.30 | 0.29 |
| $C_{22:1}$ | 0.02 | 0.02 | 0.02 | 0.01 |
| $C_{24:0}$ | 0.23 | 0.23 | 0.26 | 0.23 |
| $C_{24:1}$ | 0.14 | 0.12 | 0.14 | 0.12 |
| FDA | 6.84 | 6.84 | 6.76 | 7.06 |
| % Oil | 50.0 | 50.0 | 49.4 | 49.4 |

[1]line designation;
[2]%

Example 9

T4 Plants and T5 Seeds

T4 seeds from 10 random selfed plants representing each line selected for advancement in Example 8 were planted in a greenhouse using 5–10 seeds per row. T4 plants were selfed, and T5 seeds were collected from individual plants. A portion of the T5 seeds from each line were combined and analyzed for oil content and fatty acid analysis by NIR as described in Example 5.

Table 8 shows summary statistics (mean±standard deviation) for seed oil and seed protein content for the total T5 population, for T5 lines selected for advancement and for corresponding non-transgenic controls. Data for the Westar control plants was obtained from 5 'control samples'. Each 'control sample' contained seed bulked from approximately 20 control plants.

Forty-five T4 plants (representing 6 lines from 14 plots) from the −7ACCase/Westar transformation yielded seed having an oil content of 44.4% to 50.4% and 7 of those plants, representing 2 lines (001-30-02 and 001-31-07) yielding seed having an oil content ranging from 44.4% to 50.1%, were advanced.

TABLE 8

Oil content, protein content and fatty acid profile of T5 seeds

| | -7ACCase/Westar | | |
|---|---|---|---|
| Fatty acid | Total[1] | Sel[1] | Control[1] |
| $C_{18:1}$ | 69.00[2] | 69.40 | 68.15 |
| | (0.90) | (0.60) | (0.56) |
| $C_{18:2}$ | 13.60 | 13.20 | 14.60 |
| | (1.30) | (29.00) | (0.68) |
| $C_{18:3}$ | 7.60 | 7.80 | 7.09 |
| | (0.60) | (0.30) | (0.50) |
| % Oil | 49.90 | 49.90 | 45.64 |
| | (1.60) | (1.60) | (1.22) |
| % Protein | 20.00 | 20.50 | 24.20 |
| | (1.10) | (1.20) | (0.22) |
| Chlor[3] | 36.60 | 37.10 | 18.15 |
| | (18.20) | (25.60) | (4.86) |
| Gluc[4] | 4.80 | 4.60 | ND |
| | (1.00) | (1.10) | ND |

[1]Total, mean composition of all T4 plants; Sel, mean composition of T4 plants selected for advancement; Control, mean composition of non-transformed Westar plants;
[2]mean in percent (± standard deviation);
[3]Chlorophyl content reported in parts per million (ppm);
[4]Glucosinolate content reported in μmol/g;
ND, not determined.

Table 9 shows the fatty acid profiles of T5 seed from representative individual lines from the −7ACCase/Westar transformation that were selected for advancement.

TABLE 9

Oil content, protein content and fatty acid profile of T5 seed from representative -7ACCase/Westar lines selected for advancement

| | 001-30-02[1] | 001-30-02 | 001-30-02 | 001-31-07 |
|---|---|---|---|---|
| $C_{18:1}$ | 69.0[2] | 69.6 | 70.4 | 69.2 |
| $C_{18:2}$ | 12.6 | 12.5 | 12.3 | 14.1 |
| $C_{18:3}$ | 8.5 | 8.1 | 7.6 | 7.8 |
| % Oil | 50.3 | 50.2 | 49.8 | 52.3 |
| % Protein | 20.9 | 20.3 | 20.6 | 18.4 |
| Chlor[3] | 63.9 | 20.8 | 31.3 | 13.7 |
| Gluc[4] | 5.8 | 4.1 | 4.2 | 3.2 |

[1]line designation;
[2]%

Example 10

T5 Plants and T6 Seeds

T5 lines that were selected based on percent oil and protein content as described in Example 9 were advanced in the field in Colorado, USA and in Saskatchewan, Canada. Approximately 0.5 g of seeds from each selected line were planted and selfed. At maturity, T6 seeds were collected from 20 plants of each line and pooled for analysis of oil content and fatty acid composition by NIR. Based upon NIR analysis and favorable oil content in the pooled sample of T6 seed, T6 seed from 10 random T5 plants from each line were advanced in the greenhouse.

Two lines from the −7ACCase/Westar transformation from T5 plants grown in Canada had T6 seeds that exhibited an oil content of 38.4% to 49.5%. The protein content in seeds harvested from the Canada-grown plants was measured in air-dried, oil-free seed meal (using the 'Generic Combustion Method for Determination of Crude Protein', AOCS Method Ba 4e-93), and the mean was determined to be 46.62% (±1.33) in T6 seed from the −7ACCase/Westar transformation. Percent protein content as shown in Table 10 for the Canadian samples was estimated based upon the percent protein content reported for the air-dried, oil-free seed meal using the oil content reported and assuming a moisture content of 5%.

T5 plants representing six lines of the −7ACCase/Westar transformation grown in Colorado, USA produced seed that had an oil content of 41.9% to 51.0%, and plants from five different lines, having an oil content of 48.8% to 50.5%, were advanced.

Table 10 shows the mean oil content (±standard deviation) of the T6 plants and control plants grown in Canada, and Table 11 shows the corresponding data for the total population of T6 plants grown in the USA, those T6 plants selected for advancement and from non-transgenic control plants grown in the USA. USA-grown controls for the −7ACCase/Westar transformation consisted of 2 control samples each of IMC129 and IMC130 (IMC129 and IMC130 are both related in the following way to the Westar variety: IMC129 carries a mutation and is otherwise ≧99% Westar background, while IMC130 is the result of a cross between IMC01 and IMC129 varieties, and therefore, contains ≧50% of the Westar background). Canadian-grown controls for the −7ACCase/Wester transformation consisted of 2 IMC130 control samples.

TABLE 10

Oil content, protein content and fatty acid profile of Canadian-grown T6 seeds

| | -7ACCase/Westar | |
|---|---|---|
| | Total[1] | Control[1] |
| % Oil | 46.78[2] | 42.69 |
| | (2.88) | (0.18) |
| % Protein | 26.12[3] | 26.66[3] |

[1]Total, mean composition of all T5 plants; Control, mean composition of non-transformed Westar plants;
[2]mean in percent (± standard deviation);
[3]percent protein content was estimated based upon the percent protein content reported for the air-dried, oil-free seed meal using the oil content reported and assuming a moisture content of 5%.

TABLE 11

Oil content, protein content and fatty acid profile of USA-grown T6 seeds

| | -7ACCase/Westar | | |
|---|---|---|---|
| | Total[1] | Sel[1] | Control[1] |
| $C_{18:1}$ | 68.71[2] | 68.54 | 68.19 |
| | (1.64) | (0.77) | (6.76) |
| $C_{18:2}$ | 15.17 | 15.09 | 16.03 |
| | (1.26) | (0.78) | (5.12) |
| $C_{18:3}$ | 8.05 | 8.02 | 7.44 |
| | (0.56) | (0.23) | (2.36) |
| % Oil | 47.84 | 49.48 | 48.54 |
| | (1.45) | (0.66) | (1.65) |
| % Protein | 25.18 | 23.45 | 23.84 |
| | (1.45) | (1.09) | (1.90) |
| Chloro[3] | −3.59 | −5.67 | −0.77 |
| | (2.99) | (1.02) | (3.35) |

TABLE 11-continued

Oil content, protein content and
fatty acid profile of USA-grown T6 seeds

|  | −7ACCase/Westar | | |
|---|---|---|---|
|  | Total[1] | Sel[1] | Control[1] |
| Gluc[4] | 5.23 (0.64) | 4.87 (0.69) | 5.35 (1.24) |

[1]Total, mean composition of all T6 plants; Sel, mean composition of T6 plants selected for advancement; Control, mean composition of non-transformed Westar plants;
[2]mean in percent (± standard deviation);
[3]Chlorophyll content reported in parts per million (ppm);
[4]Glucosinolate content reported in μmol/g.

Using a one-tailed, two-sample Student's t-test, results from the T6 seeds were evaluated for statistical significance. The average oil content of the total T6 population from Canadian field plots was compared with the average oil content from the corresponding non-transgenic plants grown in Canada, while the T6 population selected for advancement from field plots in the USA was compared with the corresponding USA-grown control population for each line.

The −7ACCase/Westar plants grown in Canada (n=35) had an average oil content that was significantly higher (p<0.1) than that of the control population (n=2).

The −7ACCase/Westar plants grown in the USA and selected for advancement (n=17) had a higher oil content that was statistically significant (p<0.05) compared to the average oil content of the control plants (n=5).

Table 12 shows the percent oil content in T6 seeds from 6 representative individual lines selected for advancement from the −7ACCase/Westar transformation. Control plants grown in the field in Colorado, USA produced seeds that exhibited an average oil content of 44.62 (on a dry weight basis).

TABLE 12

Oil content of USA-grown T6 seeds from individual −7ACCase/Westar lines selected for advancement

| Line | % Oil |
|---|---|
| Tao-001-30-02 | 48.86–49.58 |
| Tao-001-31-02 | 49.93–50.51 |
| Tao-001-56-01 | 48.86–49.42 |
| Tao-001-56-06 | 48.84–50.39 |
| Tao-001-65-08 | 49.10–49.85 |

Example 11

PCR Analysis

A nickel size portion of leaf tissue was taken at 2.5 weeks post-germination from 12 T7 plants (representing 12 different −7ACCase/Westar transformed lines) grown from the T6 seeds described in Example 10. Tissue samples were dried in a food dehydrator at 135° C. for 8–16 hrs. DNA was isolated using the Qiagen Dneasy 96 Plant Kit and resuspended in 150 μl buffer.

PCR amplification was performed in a volume of 20 μl containing the following: 1×PCR Buffer containing 1.5 mM MgCl$_2$ (Qiagen PCR Core Kit); 0.2 mM dNTP; 0.5 units Taq polymerase (Qiagen); 0.5 μM MF-ACCase 119 primer (5'-GTAGGCACCCTGCTACTACA (SEQ ID NO:9)); 0.5 μM MF-ACCase 645 primer (5'-CATCAGGAATAG TAAT-CAAGTCA (SEQ ID NO:10)); 0.4% sucrose; 0.008% Cresol. A cycle amplification was performed using the following PCR conditions: denaturation at 94° C. for 30 sec, annealing at 55° C. for 30 sec, and extension at 72° C. for 60 sec. PCR products were analyzed by 1.2% agarose gel electrophoresis and visualized by ethidium bromide staining. PCR products of the predicted size were detected in all 12 −7ACCase/Westar plants analyzed, indicating the presence of the alfalfa cytosolic ACCase gene in all lines examined.

Example 12

Crosses Between the T6 Plants

T6 seeds from the selected lines shown in Table 12 were grown in the field in Colorado, USA. Reciprocal crosses were made between the T6 plants derived from the −7ACCase/Westar transformation (lacking a transit peptide) and two T6 plants derived from a +6ACCase/IMC 03 transformation (having a transit peptide). Plants were grown to maturity and the seeds were harvested. F1 seeds are grown and the resulting plants are allowed to self-pollinate. The resulting F2 progeny seeds are harvested, and the fatty acid profile is determined and oil and protein content are analyzed as described in Examples 3–5. Samples exhibiting a statistically significant increase in oil content are selected for advancement.

Example 13

Outcrosses Between the T6 Plants and Other Plant Varieties

T6 seeds from the selected lines shown in Table 12 were grown in the field in Colorado, USA. Crosses were made between the T6 plants derived from the −7ACCase/Westar transformation (lacking a transit peptide) or two T6 plants derived from a +6ACCase/IMC 03 transformation (having a transit peptide) and plants of a Brassica line exhibiting high oleic acid content. An example of a high oleic acid Brassica variety is Q4275, described in PCT 96/20090. F1 seeds are grown and the resulting plants are allowed to self-pollinate. The resulting F2 progeny seeds are harvested, and the fatty acid profile is determined and oil and protein content are analyzed as described in Examples 3–5. Samples exhibiting a statistically significant increase in oil content, as well as high oleic acid content, are selected for advancement.

T6 seeds from the selected lines shown in Table 12 were grown in the field in Colorado, USA. Crosses were made between the T6 plants derived from the −7ACCase/Westar transformation (lacking a transit peptide) or two T6 plants derived from a +6ACCase/IMC 03 transformation (having a transit peptide) and plants of a Brassica line exhibiting elevated oil content but lacking an ACCase construct. Examples of Brassica varieties exhibiting elevated oil are IMC106RR and IMC107RR, proprietary Cargill Brassica lines. The oil content in IMC106RR or IMC107RR is about 46.5–47% and 47.5–48%, respectively, on a dry weight basis. Another example of a Brassica line that exhibits elevated oil content is Polo, a non-transgenic variety registered in Canada (Registration #AG012). Polo has an oil content of about 48.5–49.5% on a dry weight basis. F1 seeds were grown in the greenhouse and the resulting plants allowed to self-pollinate. The resulting F2 progeny seeds are harvested, and the fatty acid profile is determined and oil and protein content are analyzed as described in Examples 3–5. Seeds exhibiting an oil content that is significantly higher than either parental line are selected for advancement. Progeny plants are allowed to self-pollinate and the seeds analyzed for oil content. Those seeds exhibiting increased oil content are advanced.

T6 seeds from the selected lines shown in Table 12 were grown in the field in Colorado, USA. Crosses were made between the T6 plants derived from the −7ACCase/Westar transformation (lacking a transit peptide) or two T6 plants derived from a +6ACCase/IMC 03 transformation (having a transit peptide) and plants of a Brassica line exhibiting high erucic acid content but lacking an ACCase construct. Suitable high erucic acid Brassica lines include, for example, Hero (HE101, HEC01), Mercury, Venus or Neptune which have about 45% or more erucic acid (McVetty et al., *Can. J. Plant Sci.*, 76(2):341–342 (1996); Scarth et al., *Can. J. Plant Sci.*, 75(1):205–206 (1995); and McVetty et al., *Can J. Plant Sci.*, 76(2):343–344 (1996)). F1 seeds were grown in the greenhouse and the resulting plants allowed to self-pollinate. The resulting F2 progeny seeds are harvested, and the fatty acid profile is determined and oil and protein content are analyzed as described in Examples 3–5. Seeds exhibiting an oil content that is significantly higher than either parental line are selected for advancement. Progeny plants are allowed to self-pollinate and the seeds analyzed for oil content. Those seeds exhibiting increased oil content are advanced.

Additionally, PCR is used to examine the segregation of the alfalfa ACCase nucleic acid in the progeny of the above-described crosses. After crossing T6 plants derived from a −7ACCase/Westar transformation or T6 plants derived from a +6ACCase/IMC 03 transformation with an appropriate plant (ie., a plant exhibiting high oil, high oleic acid or high erucic acid), F1 seeds are harvested, grown in the greenhouse and the resulting plants are allowed to self-pollinate. The resulting F2 progeny seeds are harvested, and PCR is performed to detect the presence of the alfalfa ACCase nucleic acid sequences using DNA extracted from the seed. Alternatively, the F2 seeds are grown into mature F3 plants, and PCR is performed, using DNA extracted from the leaves of the plant to detect the presence of the alfalfa ACCase nucleic acid sequences. Representative PCR primers homologous to the alfalfa ACCase are described in Example 11. If PCR amplification indicates the presence of the alfalfa ACCase nucleic acid sequences, oil content is then determined by NMR or NIR as described in Examples 4 and 5. Seeds or plants are subsequently advanced based upon a positive PCR amplification (i.e., the presence of the alfalfa ACCase nucleic acid sequences) and elevated oil content.

Example 14

Increased Oil Content in Crushed Seeds

T6 seeds of Example 10 are planted, allowed to pollinate, and the resulting seeds are harvested and crushed. The oil content of the crushed seeds is about 5% to about 25% higher than the oil content in a corresponding plant lacking an ACCase construct. The oil is extracted from the crushed seeds as described in, e.g., U.S. Pat. No. 5,969,169 or 5,850,026.

Briefly, the seed is cleaned through commercial seed cleaning equipment to remove foreign matter such as weed seeds, plant material, immature seed and other matter. The cleaned seed is crushed and the resulting oil is processed at the Cargill Plant (West Fargo, N.Dak.). Greater than 350 tons of seed is crushed using the processing conditions outlined below.

Whole seed is passed through a double roll Bauermeister flaking rolls with smooth surface rolls available from Bauermeister Inc. (Memphis, Tenn.). The roll gap is adjusted so as to produce a flake 0.25 to 0.30 mm in thickness. Flaked seed is conveyed to a five-tray, 8-foot diameter stacked cooker, manufactured by Crown Iron Works (Minneapolis, Minn.). The flaked seed moisture is adjusted in the stacked cooker to 5.5–6.0%. Indirect heat from the steam heated cooker trays is used to progressively increase the seed flake temperature to 80–90° C., with a retention time of approximately 20–30 minutes. A mechanical sweep arm in the stacked cooker is used to ensure uniform heating of the seed flakes. Heat is applied to the flakes to deactivate enzymes, facilitate further cell rupturing, coalesce the oil droplets and agglomerate protein particles in order to ease the extraction process.

Heated flakes are conveyed to a screw press from Anderson International Corp. (Cleveland, Ohio) equipped with a suitable screwworm assembly to reduce press out of the oil from the flakes by approximately 70%. The resulting press cake contains a small percentage of residual oil. Crude oil produced from the pressing operation is passe through a settling tank with a slotted wire drainage top to remove the solids expressed out with the oil in the screw pressing operation. The clarified oil is passed through a plate and frame filter to remove the remaining fine solid particles. The filtered oil is combined with the oil recovered from the extraction process before oil refining.

The press cake produced from the screw pressing operation is transferred to a FOMM basket extractor available from French Oil Mill and Machinery Co. (Piqua, Ohio) where the oil remaining in the cake is extracted with commercial n-hexane at 55° C. Multiple counter-current hexane washes are used to substantially remove the remaining oil in the press cake, resulting in a press cake that contains residual oil in the extracted cake. The oil and hexane mixture (miscella) from the extraction process is passed through a two-stage rising film tube type distillation column to distill the hexane from the oil. Final hexane removal from the oil is achieved by passing the oil through a stripper column containing disk and doughnut internals under 23–26 in Hg vacuum and at 107–115° C. A small amount of stripping steam is used to facilitate the hexane removal. The oil recovered from the extraction process is combined with the filtered oil from the screw pressing operation, resulting in blended crude oil, and is transferred to oil processing.

In the oil processing, the crude oil is heated to 66° C. in a batch-refining tank, to which 0.15% food-grade phosphoric acid, as 85% phosphoric acid, is added. The acid serves to convert the non-hydratable phosphatides to a hydratable form, and to chelate minor metals that are present in the crude oil. The phosphatides and the metal salts are removed from the oil along with the soapstock. After mixing for 60 minutes at 66° C., the oil acid mixture is treated with sufficient sodium hydroxide solution to neutralize the free fatty acids and the phosphoric acid in the acid oil mixture. This mixture is heated to 71° C. and mixed for 35 minutes. The agitation is stopped and the neutralized free fatty acids, phosphatides, etc. (soapstock) are allowed to settle into the cone bottom of the refining tank for 6 hours. After the settling period, the soapstock is drained off from the neutralized oil.

A water wash is done to reduce the soap content of the oil by heating the oil to 82° C. and adding 12% hot water. Agitation of the mixture continues for 10 minutes. The mixture is allowed to settle out for 4 hours, at which time the water is drained off the bottom of the refining vessel. The water washed oil is heated to 104–110° C. in a vacuum bleacher vessel maintained at 24–26 in. Hg vacuum. A slurry of the oil and Clarion 470 bleaching clay available from American Colloid Company (Refining Chemicals Division, Arlington Heights, Ill.) is added to the oil in the vacuum bleacher. This mixture is agitated for 20 minutes before filtering to remove the bleaching clay. The clay slurry addition is adjusted to provide a Lovibond color (AOCS Official Method Cc 136-4) of less than 1.0 red units when the oil is heated to 288° C. under atmospheric pressure. Nitrogen is injected into the filtered bleached oil and is maintained under a nitrogen blanket until the oil is deodorized.

Refined and bleached oil is deodorized in a semi-continuous Votator deodorizer tower at a rate of approximately 7,000 pounds per hour. The deodorization temperature is maintained at 265–268° C. with a system pressure of 0.3–0.5 mm Hg absolute pressure. Sparge steam is used to strip off the free fatty acids, color bodies, and odor components. Retention time in the deodorizer is generally 30–90 minutes. The deodorized oil is cooled to 45–50° C. and nitrogen is injected prior to removal of the vacuum. The deodorized oil is stored under a nitrogen blanket and the resulting deodorized oil analyzed for fatty acid composition.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A plant containing a recombinant nucleic acid construct comprising a nucleic acid encoding a cytosolic ACCase operably linked to a promoter, wherein said construct lacks a nucleic acid encoding a transit peptide operably linked to said nucleic acid encoding said cytosolic ACCase, wherein said plant produces seeds that exhibit a statistically significant increase in oil content as compared to seeds produced by a corresponding plant lacking said nucleic acid construct, wherein said increase in oil content is from about 5% to about 25% on a dry weight basis.

2. The plant of claim 1, wherein said nucleic acid encodes a plant cytosolic ACCase.

3. The plant of claim 2, wherein said nucleic acid encodes an alfalfa cytosolic ACCase.

4. The plant of claim 1, wherein said nucleic acid encoding said ACCase lacks introns.

5. The plant of claim 1, wherein said promoter is a cauliflower mosaic virus (CaMV) 35S promoter.

6. The plant of claim 5, wherein said nucleic acid encoding said cytosolic ACCase lacks introns.

7. The plant of claim 1, wherein said plant is a soybean plant.

8. The plant of claim 1, wherein said plant is a Brassica plant.

9. The plant of claim 8, wherein said plant is selected from the group consisting of *Brassica napus, Brassica rapa, Brassica juncea, Brassica carinata, Brassica nigra* and *Brassica oleracea*.

10. Seeds produced by the plant of claim 1.

11. Progeny of the plant of claim 1, wherein said progeny produce seeds that exhibit said statistically significant increase in oil content.

12. A method of producing a plant, comprising:
    (a) providing a plant comprising a nucleic acid construct comprising a nucleic acid encoding a cytosolic ACCase operably linked to a promoter, wherein said construct lacks a nucleic acid encoding a transit peptide operably linked to said nucleic acid encoding said cytosolic ACCase; and
    (b) selecting, for at least one generation, progeny plants that produce seeds exhibiting a statistically significant increase in oil content as compared to seeds produced by a corresponding plant lacking said nucleic acid construct, wherein said increase in oil content is from about 5% to about 25% on a dry weight basis.

13. The method of claim 12, wherein said nucleic acid encodes a plant cytosolic ACCase.

14. The method of claim 13, wherein said nucleic acid encodes an alfalfa cytosolic ACCase.

15. The method of claim 12, wherein said nucleic acid encoding said cytosolic ACCase lacks introns.

16. The method of claim 12, wherein said promoter is a CaMV 35S promoter.

17. The method of claim 12, herein said selecting is for at least three generations.

18. The method of claim 12, wherein said plant is a Brassica plant.

19. The method of claim 18, wherein said plant is selected from the group consisting of *Brassica napus, Brassica rapa, Brassica juncea, Brassica carinata, Brassica nigra* and *Brassica oleracea*.

20. A method of producing a plant, comprising the step of:
    (a) introducing a construct into one or more plants, said construct comprising a nucleic acid encoding a cytosolic acetyl ACCase operably linked to a promoter, wherein said construct lacks a nucleic acid encoding a transit peptide operably linked to said nucleic acid encoding said cytosolic ACCase,
    wherein progeny of one or more of said transgenic plants, following at least one generation of selection, produce seeds that exhibit a statistically significant increase in oil content as compared to seeds produced by a corresponding plant lacking said nucleic acid encoding said ACCase, wherein said increase in oil content is from about 5% to about 25% on a dry weight basis.

21. A method of increasing the oil content in seeds, comprising the steps of:
    (a) creating one or more plants containing a nucleic acid construct, said nucleic acid construct comprising a nucleic acid encoding a cytosolic ACCase operably linked to a promoter, wherein said construct lacks a nucleic acid encoding a transit peptide operably linked to said nucleic acid encoding said cytosolic ACCase; and
    (b) selecting progeny of said one or more plants that exhibit a statistically significant increase in oil content in seeds as compared to seeds produced by a corresponding plant lacking said nucleic acid encoding said ACCase, wherein said increase in oil content is from about 5% to about 25% on a dry weight basis.

22. The method of claim 21, wherein said selection step comprises selecting progeny that contain said nucleic acid construct.

* * * * *

SEQUENCE LISTING

<160> NUMBER OF SEQ ID NOS: 12

<210> SEQ ID NO 1
<211> LENGTH: 56
<212> TYPE: DNA
<213> ORGANISM: Artificial Sequence
<220> FEATURE:
<223> OTHER INFORMATION: primer for PCR

<400> SEQUENCE: 1
caucaucauc auatcgatag gtaccaaaaa aaacaaccat ggcttcctca gttctt        56

<210> SEQ ID NO 2
<211> LENGTH: 45
<212> TYPE: DNA
<213> ORGANISM: Artificial Sequence
<220> FEATURE:
<223> OTHER INFORMATION: primer for PCR

<400> SEQUENCE: 2
cuacuacuac uagctagcca tggacttctt gttaattggt ggcca                   45

<210> SEQ ID NO 3
<211> LENGTH: 204
<212> TYPE: DNA
<213> ORGANISM: Nicotiana tabacum
<220> FEATURE:
<221> NAME/KEY: CDS
<222> LOCATION: (1)...(204)

<400> SEQUENCE: 3

```
atg gct tcc tca gtt ctt tcc tct gca gca gtt gcc acc cgc agc aat        48
Met Ala Ser Ser Val Leu Ser Ser Ala Ala Val Ala Thr Arg Ser Asn
 1               5                  10                  15 gtt gct caa gct aac atg gtt gca cct ttc act ggc ctt aag tca gct        96
Val Ala Gln Ala Asn Met Val Ala Pro Phe Thr Gly Leu Lys Ser Ala
            20                  25                  30 gcc tca ttc cct gtt tca agg aag caa aac ctt gac atc act tcc att       144
Ala Ser Phe Pro Val Ser Arg Lys Gln Asn Leu Asp Ile Thr Ser Ile
        35                  40                  45 gcc agc aac ggc gga aga gtg caa tgc atg cag gtg tgg cca cca att       192
Ala Ser Asn Gly Gly Arg Val Gln Cys Met Gln Val Trp Pro Pro Ile
    50                  55                  60 aac aag aag tcc                                                       204
Asn Lys Lys Ser
 65
```

<210> SEQ ID NO 4
<211> LENGTH: 68
<212> TYPE: PRT
<213> ORGANISM: Nicotiana tabacum

<400> SEQUENCE: 4

```
Met Ala Ser Ser Val Leu Ser Ser Ala Ala Val Ala Thr Arg Ser Asn
 1               5                  10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys Met Gln Val Trp Pro Pro Ile
    50                  55                  60

Asn Lys Lys Ser
65
```

<210> SEQ ID NO 5
<211> LENGTH: 149
<212> TYPE: DNA
<213> ORGANISM: Artificial Sequence
<220> FEATURE:
<223> OTHER INFORMATION: representative construct (5' end)

<400> SEQUENCE: 5

| ctaacatggt tgcacctttc actggcctta agtcagctgc ctcattccct gtttcaagga | 60 |
| agcaaaacct tgacatcact tccattgcca gcaacggcgg aagagtgcaa tgcatgcagg | 120 |
| tgtggccacc aattaacaag aagtccatg | 149 |

<210> SEQ ID NO 6
<211> LENGTH: 22
<212> TYPE: DNA
<213> ORGANISM: Artificial Sequence
<220> FEATURE:
<223> OTHER INFORMATION: representative construct (5' end)

<400> SEQUENCE: 6

| ggtaccaaaa aaacaacca tg | 22 |

<210> SEQ ID NO 7
<211> LENGTH: 7151
<212> TYPE: DNA
<213> ORGANISM: Medicago sativa
<220> FEATURE:
<221> NAME/KEY: CDS
<222> LOCATION: (1)...(6771)

<400> SEQUENCE: 7

```
atg gct agc gtg ggc cgt gga aat gga tat tta aac agt gtg cta ccg    48
Met Ala Ser Val Gly Arg Gly Asn Gly Tyr Leu Asn Ser Val Leu Pro
 1               5                  10                  15 agt agg cac cct gct act aca acc gaa gta gat gaa tac tgc aat gcc    96
Ser Arg His Pro Ala Thr Thr Thr Glu Val Asp Glu Tyr Cys Asn Ala
            20                  25                  30 ctt gga gga aac aag ccg att cat agc ata ttg att gca aac aat gga   144
Leu Gly Gly Asn Lys Pro Ile His Ser Ile Leu Ile Ala Asn Asn Gly
        35                  40                  45 atg gca gca gtc aag ttt ata cgt agt gtt agg agt tgg gct tac gag   192
Met Ala Ala Val Lys Phe Ile Arg Ser Val Arg Ser Trp Ala Tyr Glu
    50                  55                  60
```

-continued

```
aca ttt ggc acg gaa aaa gct atc ttg ttg gtt gcc atg gca act cca    240
Thr Phe Gly Thr Glu Lys Ala Ile Leu Leu Val Ala Met Ala Thr Pro
 65                  70                  75                  80 gag gat atg aga atc aat gca gaa cat atc aga ata gcc gat caa ttt    288
Glu Asp Met Arg Ile Asn Ala Glu His Ile Arg Ile Ala Asp Gln Phe
                 85                  90                  95 gtg gaa gta cct ggt ggg acc aat aac aat aac tac gcc aat gtg cag    336
Val Glu Val Pro Gly Gly Thr Asn Asn Asn Asn Tyr Ala Asn Val Gln
            100                 105                 110 ctt att cta gag att gct gag ata act cac gtt gat gcg gtg tgg cct    384
Leu Ile Leu Glu Ile Ala Glu Ile Thr His Val Asp Ala Val Trp Pro
        115                 120                 125 ggt tgg ggt cat gca tca gaa aat cct gag ctt cca gat gca tta aaa    432
Gly Trp Gly His Ala Ser Glu Asn Pro Glu Leu Pro Asp Ala Leu Lys
    130                 135                 140 gca aag gga att gta ttc ctt gga cct cct gct ata tct atg gca gca    480
Ala Lys Gly Ile Val Phe Leu Gly Pro Pro Ala Ile Ser Met Ala Ala
145                 150                 155                 160 ttg gga gac aaa att ggt tcc tcg ttg att gct cag gca gca gaa gtt    528
Leu Gly Asp Lys Ile Gly Ser Ser Leu Ile Ala Gln Ala Ala Glu Val
                165                 170                 175 cca acc ctt cca tgg agt ggt tct cat gtg aaa att cct cca gaa agt    576
Pro Thr Leu Pro Trp Ser Gly Ser His Val Lys Ile Pro Pro Glu Ser
            180                 185                 190 gac ttg att act att cct gat gaa att tac cgt gca gca tgt gtt tat    624
Asp Leu Ile Thr Ile Pro Asp Glu Ile Tyr Arg Ala Ala Cys Val Tyr
        195                 200                 205 aca aca gaa gaa gca att gca agt tgt caa gta gta ggt tac cct gca    672
Thr Thr Glu Glu Ala Ile Ala Ser Cys Gln Val Val Gly Tyr Pro Ala
    210                 215                 220 atg att aag gca tct tgg ggt ggt ggc ggc aaa ggc ata aga aag gtt    720
Met Ile Lys Ala Ser Trp Gly Gly Gly Gly Lys Gly Ile Arg Lys Val
225                 230                 235                 240 cat aat gat gat gag gtt agg gca ttg ttc aag caa gtt caa ggt gaa    768
His Asn Asp Asp Glu Val Arg Ala Leu Phe Lys Gln Val Gln Gly Glu
                245                 250                 255 gta cca ggc tca cct ata ttt ata atg aaa gtt gct tcc cag agc cga    816
Val Pro Gly Ser Pro Ile Phe Ile Met Lys Val Ala Ser Gln Ser Arg
            260                 265                 270 cat ctt gaa gtc caa ttg att tgc gat cag cac gga aat ttt gca gca    864
His Leu Glu Val Gln Leu Ile Cys Asp Gln His Gly Asn Phe Ala Ala
        275                 280                 285 ttg cac agc cgt gat tgt agt gtt caa aga agg cat caa aag att att    912
Leu His Ser Arg Asp Cys Ser Val Gln Arg Arg His Gln Lys Ile Ile
    290                 295                 300 gaa gag ggt ccc att act gta gca cct cca gaa acg gtg aaa gaa ctt    960
Glu Glu Gly Pro Ile Thr Val Ala Pro Pro Glu Thr Val Lys Glu Leu
305                 310                 315                 320 gaa cag gcg gct aga aga tta gct aaa tct gta aat tat gtg ggg gca    1008
Glu Gln Ala Ala Arg Arg Leu Ala Lys Ser Val Asn Tyr Val Gly Ala
                325                 330                 335 gct acc gtt gag tat ctt tat agc atg gaa act ggc gag tac tac ttt    1056
Ala Thr Val Glu Tyr Leu Tyr Ser Met Glu Thr Gly Glu Tyr Tyr Phe
            340                 345                 350 tta gag ttg aac ccc cga cta cag gtt gag cat cct gtt act gaa tgg    1104
Leu Glu Leu Asn Pro Arg Leu Gln Val Glu His Pro Val Thr Glu Trp
        355                 360                 365 ata gct gag ata aat ctg cca gca gca caa gtt gca gtt ggg atg ggc    1152
Ile Ala Glu Ile Asn Leu Pro Ala Ala Gln Val Ala Val Gly Met Gly
    370                 375                 380
```

```
atc cca ctc tgg caa att cct gag att agg cgt ttc tat ggg atg gaa      1200
Ile Pro Leu Trp Gln Ile Pro Glu Ile Arg Arg Phe Tyr Gly Met Glu
385                 390                 395                 400 cat ggt ggg gga aat gat ggt tgg aag aaa aca tca gtg tta gct acc      1248
His Gly Gly Gly Asn Asp Gly Trp Lys Lys Thr Ser Val Leu Ala Thr
                405                 410                 415 cct ttt gat ttt gac gaa gca caa tct aca aag ccg aaa ggt cat tgt      1296
Pro Phe Asp Phe Asp Glu Ala Gln Ser Thr Lys Pro Lys Gly His Cys
            420                 425                 430 gtg gct gta cga gtc acc agt gag gac ccc gat gat ggt ttt acg cct      1344
Val Ala Val Arg Val Thr Ser Glu Asp Pro Asp Asp Gly Phe Thr Pro
        435                 440                 445 aca gga gga aaa gtg cag gag ctc agc ttt aaa agc aag cca aat gtg      1392
Thr Gly Gly Lys Val Gln Glu Leu Ser Phe Lys Ser Lys Pro Asn Val
    450                 455                 460 tgg gct tat ttc tct gtt aag tcc gga gga gga att cat gaa ttc tca      1440
Trp Ala Tyr Phe Ser Val Lys Ser Gly Gly Gly Ile His Glu Phe Ser
465                 470                 475                 480 gat tct caa ttt gga cat gtt ttt gcg ttt gga gaa tct aga gct tta      1488
Asp Ser Gln Phe Gly His Val Phe Ala Phe Gly Glu Ser Arg Ala Leu
                485                 490                 495 gca att gca aat atg gta ctg ggg ttg aag gaa att caa att cga gga      1536
Ala Ile Ala Asn Met Val Leu Gly Leu Lys Glu Ile Gln Ile Arg Gly
            500                 505                 510 gaa att cgt acc aac gtt gat tac aca att gat ctt ctg aat gct tca      1584
Glu Ile Arg Thr Asn Val Asp Tyr Thr Ile Asp Leu Leu Asn Ala Ser
        515                 520                 525 gac tac aga gac aac aaa att cac aca gga tgg cta gac agt aga att      1632
Asp Tyr Arg Asp Asn Lys Ile His Thr Gly Trp Leu Asp Ser Arg Ile
    530                 535                 540 gca atg cgg gtt aga gca gag agg cct ccc tgg tat ctg tct gtt gtt      1680
Ala Met Arg Val Arg Ala Glu Arg Pro Pro Trp Tyr Leu Ser Val Val
545                 550                 555                 560 ggt ggg gca ctc tat aaa gct tct gcc agc agt gca gct tta gtt tcg      1728
Gly Gly Ala Leu Tyr Lys Ala Ser Ala Ser Ser Ala Ala Leu Val Ser
                565                 570                 575 gac tat gtt ggc tat ctt gaa aag ggg caa atc cct ccc aag cac att      1776
Asp Tyr Val Gly Tyr Leu Glu Lys Gly Gln Ile Pro Pro Lys His Ile
            580                 585                 590 tct ctt gtc cat tct caa gtt tct ttg agc att gaa gga agc aaa tac      1824
Ser Leu Val His Ser Gln Val Ser Leu Ser Ile Glu Gly Ser Lys Tyr
        595                 600                 605 acg att gac atg gta cga gga gga cct gga agt tac aaa ttg aaa ttg      1872
Thr Ile Asp Met Val Arg Gly Gly Pro Gly Ser Tyr Lys Leu Lys Leu
    610                 615                 620 aat caa tcg gag ata gaa gcg gag ata cac act tta cgt gat gga ggt      1920
Asn Gln Ser Glu Ile Glu Ala Glu Ile His Thr Leu Arg Asp Gly Gly
625                 630                 635                 640 ttg cta atg cag ttg gat gga aac agt cat gta ata tat gca gag gaa      1968
Leu Leu Met Gln Leu Asp Gly Asn Ser His Val Ile Tyr Ala Glu Glu
                645                 650                 655 gaa gca gct gga act cgg ctt tta ata gat gga agg act tgc ttg ctt      2016
Glu Ala Ala Gly Thr Arg Leu Leu Ile Asp Gly Arg Thr Cys Leu Leu
            660                 665                 670 cag aat gat gac gat cca tca aag tta att gga gag aca ccg tgc aag      2064
Gln Asn Asp Asp Asp Pro Ser Lys Leu Ile Gly Glu Thr Pro Cys Lys
        675                 680                 685 ctt ctg aga tat ttg gtt gcg gat gat agt cag att gat gca gac aca      2112
Leu Leu Arg Tyr Leu Val Ala Asp Asp Ser Gln Ile Asp Ala Asp Thr
```

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     | 690 |     |     |     | 695 |     |     |     | 700 |     |     |     |      |
| cca | tat | gct | gaa | gtt | gag | gtc | atg | aag | atg | tgc | atg | cct | ctt | ctt | tcc  | 2160 |
| Pro | Tyr | Ala | Glu | Val | Glu | Val | Met | Lys | Met | Cys | Met | Pro | Leu | Leu | Ser  |
| 705 |     |     |     |     | 710 |     |     |     |     | 715 |     |     |     |     | 720  |

| cct | gct | tct | gga | att | att | cat | ttc | aga | atg | gct | gaa | ggt | caa | gcc | atg | 2208 |
| Pro | Ala | Ser | Gly | Ile | Ile | His | Phe | Arg | Met | Ala | Glu | Gly | Gln | Ala | Met |
|     |     |     |     | 725 |     |     |     |     | 730 |     |     |     |     | 735 |     |

| cag | gct | ggt | gaa | ctt | ata | gca | aag | ctt | gat | cta | gat | gat | ggt | tct | gca | 2256 |
| Gln | Ala | Gly | Glu | Leu | Ile | Ala | Lys | Leu | Asp | Leu | Asp | Asp | Gly | Ser | Ala |
|     |     |     | 740 |     |     |     |     | 745 |     |     |     |     | 750 |     |     |

| gta | agg | aag | gca | gaa | ccc | ttc | act | ggg | agc | ttc | cct | atc | ctg | ggc | cct | 2304 |
| Val | Arg | Lys | Ala | Glu | Pro | Phe | Thr | Gly | Ser | Phe | Pro | Ile | Leu | Gly | Pro |
|     |     | 755 |     |     |     |     | 760 |     |     |     |     | 765 |     |     |     |

| cct | act | gca | att | tca | ggt | aaa | gtt | cat | cag | aaa | tgt | gca | gca | agc | tta | 2352 |
| Pro | Thr | Ala | Ile | Ser | Gly | Lys | Val | His | Gln | Lys | Cys | Ala | Ala | Ser | Leu |
| 770 |     |     |     |     | 775 |     |     |     |     | 780 |     |     |     |     |     |

| aac | gct | gca | cgg | atg | att | ctt | gct | ggc | tat | gag | cac | aac | att | gat | gaa | 2400 |
| Asn | Ala | Ala | Arg | Met | Ile | Leu | Ala | Gly | Tyr | Glu | His | Asn | Ile | Asp | Glu |
| 785 |     |     |     |     | 790 |     |     |     |     | 795 |     |     |     |     | 800 |

| gtt | gtg | gtc | aaa | agt | ttg | ctc | aat | tgc | ctt | gac | agc | cct | gaa | ctg | cct | 2448 |
| Val | Val | Val | Lys | Ser | Leu | Leu | Asn | Cys | Leu | Asp | Ser | Pro | Glu | Leu | Pro |
|     |     |     |     | 805 |     |     |     |     | 810 |     |     |     |     | 815 |     |

| ttc | ctt | caa | tgg | caa | gag | tgc | ttt | gca | gtt | ttg | gca | acc | cgt | ctt | ccc | 2496 |
| Phe | Leu | Gln | Trp | Gln | Glu | Cys | Phe | Ala | Val | Leu | Ala | Thr | Arg | Leu | Pro |
|     |     |     | 820 |     |     |     |     | 825 |     |     |     |     | 830 |     |     |

| aaa | gat | ctt | aga | aac | gag | ttg | gaa | gct | aaa | tat | aag | gag | ttc | gaa | att | 2544 |
| Lys | Asp | Leu | Arg | Asn | Glu | Leu | Glu | Ala | Lys | Tyr | Lys | Glu | Phe | Glu | Ile |
|     |     | 835 |     |     |     |     | 840 |     |     |     |     | 845 |     |     |     |

| att | tca | agc | tcc | caa | act | att | gat | ttc | cct | gcc | aaa | tta | ttg | aag | gca | 2592 |
| Ile | Ser | Ser | Ser | Gln | Thr | Ile | Asp | Phe | Pro | Ala | Lys | Leu | Leu | Lys | Ala |
| 850 |     |     |     |     | 855 |     |     |     |     | 860 |     |     |     |     |     |

| atc | ctt | gaa | gct | cat | ctt | tcc | tcc | tgt | cct | gaa | aac | gaa | aaa | gga | gcc | 2640 |
| Ile | Leu | Glu | Ala | His | Leu | Ser | Ser | Cys | Pro | Glu | Asn | Glu | Lys | Gly | Ala |
| 865 |     |     |     |     | 870 |     |     |     |     | 875 |     |     |     |     | 880 |

| tta | gaa | aga | cta | gtt | gaa | ccg | ctg | aca | agt | ctt | gta | aag | tct | tat | gag | 2688 |
| Leu | Glu | Arg | Leu | Val | Glu | Pro | Leu | Thr | Ser | Leu | Val | Lys | Ser | Tyr | Glu |
|     |     |     |     | 885 |     |     |     |     | 890 |     |     |     |     | 895 |     |

| ggt | gga | aga | gag | agc | cat | gct | cat | aaa | att | gtt | caa | tct | cta | ttt | gaa | 2736 |
| Gly | Gly | Arg | Glu | Ser | His | Ala | His | Lys | Ile | Val | Gln | Ser | Leu | Phe | Glu |
|     |     |     | 900 |     |     |     |     | 905 |     |     |     |     | 910 |     |     |

| gag | tat | ctt | tca | gtt | gaa | gaa | cta | ttc | agt | gat | aat | ata | cag | gct | gat | 2784 |
| Glu | Tyr | Leu | Ser | Val | Glu | Glu | Leu | Phe | Ser | Asp | Asn | Ile | Gln | Ala | Asp |
|     |     | 915 |     |     |     |     | 920 |     |     |     |     | 925 |     |     |     |

| gta | att | gaa | cga | ctc | cgt | ctt | caa | tac | aag | aaa | gat | ttg | ttg | aag | att | 2832 |
| Val | Ile | Glu | Arg | Leu | Arg | Leu | Gln | Tyr | Lys | Lys | Asp | Leu | Leu | Lys | Ile |
|     |     | 930 |     |     |     |     | 935 |     |     |     |     | 940 |     |     |     |

| gta | gat | att | gtg | ctc | tct | cat | cag | ggt | gtc | aag | agc | aaa | aac | aag | ctg | 2880 |
| Val | Asp | Ile | Val | Leu | Ser | His | Gln | Gly | Val | Lys | Ser | Lys | Asn | Lys | Leu |
| 945 |     |     |     |     | 950 |     |     |     |     | 955 |     |     |     |     | 960 |

| ata | ctg | cga | cta | atg | gat | aaa | ctg | gtt | tac | cct | aat | cct | gct | gcc | tat | 2928 |
| Ile | Leu | Arg | Leu | Met | Asp | Lys | Leu | Val | Tyr | Pro | Asn | Pro | Ala | Ala | Tyr |
|     |     |     |     | 965 |     |     |     |     | 970 |     |     |     |     | 975 |     |

| agg | gat | caa | tta | atc | cga | ttc | tcc | caa | ctc | aac | cat | ata | gtt | tat | tct | 2976 |
| Arg | Asp | Gln | Leu | Ile | Arg | Phe | Ser | Gln | Leu | Asn | His | Ile | Val | Tyr | Ser |
|     |     |     | 980 |     |     |     |     | 985 |     |     |     |     | 990 |     |     |

| gag | ttg | gct | ctt | aag | gca | agt | caa | ctg | ttg | gag | caa | act | aaa | ctc | agt | 3024 |
| Glu | Leu | Ala | Leu | Lys | Ala | Ser | Gln | Leu | Leu | Glu | Gln | Thr | Lys | Leu | Ser |
|     |     |     |     | 995 |     |     |     |    1000 |     |     |     |    1005 |     |     |     |

| gaa | ctt | cga | tcc | agc | att | gct | aga | agt | ctt | tct | gaa | cta | gaa | atg | ttt | 3072 |

-continued

| | | |
|---|---|---|
| Glu Leu Arg Ser Ser Ile Ala Arg Ser Leu Ser Glu Leu Glu Met Phe<br>    1010                    1015                  1020 | | |
| acc gag gat ggt gaa aat att gat act ccg aag agg aag agt gcc att<br>Thr Glu Asp Gly Glu Asn Ile Asp Thr Pro Lys Arg Lys Ser Ala Ile<br>1025                  1030                  1035                  1040 | 3120 |
| aat gac aga atg gag gac ctt gtg agc gct cct ttg gct gtt gaa gat<br>Asn Asp Arg Met Glu Asp Leu Val Ser Ala Pro Leu Ala Val Glu Asp<br>                  1045                  1050                  1055 | 3168 |
| gcc ctt gtt ggt tta ttt gat cac agc gat cac acc ctt caa agg aga<br>Ala Leu Val Gly Leu Phe Asp His Ser Asp His Thr Leu Gln Arg Arg<br>1060                  1065                  1070 | 3216 |
| gtt gtt gaa act tat atc cgt agg ctc tat cag cca tat ctt gtc aaa<br>Val Val Glu Thr Tyr Ile Arg Arg Leu Tyr Gln Pro Tyr Leu Val Lys<br>              1075                  1080                  1085 | 3264 |
| gat agc atc agg atg cag tgg cac aga tct ggc ctt att gct aca tgg<br>Asp Ser Ile Arg Met Gln Trp His Arg Ser Gly Leu Ile Ala Thr Trp<br>    1090                  1095                  1100 | 3312 |
| gaa ttc tta gaa gaa tac gtt gaa cgg aag aat ggg gtt gaa gac aaa<br>Glu Phe Leu Glu Glu Tyr Val Glu Arg Lys Asn Gly Val Glu Asp Lys<br>1105                  1110                  1115                  1120 | 3360 |
| aca ctg gtg gag aaa cat agt gag aag aaa tgg gga gtg atg gtt gta<br>Thr Leu Val Glu Lys His Ser Glu Lys Lys Trp Gly Val Met Val Val<br>                  1125                  1130                  1135 | 3408 |
| att aaa tct ctt cag ttt ttg cca gca att atc agt gct gca tta aga<br>Ile Lys Ser Leu Gln Phe Leu Pro Ala Ile Ile Ser Ala Ala Leu Arg<br>              1140                  1145                  1150 | 3456 |
| gaa gca acc aat aac ttt cac gat cct ctt aaa agt ggt tct ggt gac<br>Glu Ala Thr Asn Asn Phe His Asp Pro Leu Lys Ser Gly Ser Gly Asp<br>    1155                  1160                  1165 | 3504 |
| tca agt aac cat ggt aat atg atg cat att gga tta gtg ggg atc aac<br>Ser Ser Asn His Gly Asn Met Met His Ile Gly Leu Val Gly Ile Asn<br>1170                  1175                  1180 | 3552 |
| aac caa atg agt tta ctt caa gac agt ggt gat gag gat cag gct caa<br>Asn Gln Met Ser Leu Leu Gln Asp Ser Gly Asp Glu Asp Gln Ala Gln<br>1185                  1190                  1195                  1200 | 3600 |
| gaa aga att gat aag ttg gcc aaa ata ctc aga gag cag gaa ata ggg<br>Glu Arg Ile Asp Lys Leu Ala Lys Ile Leu Arg Glu Gln Glu Ile Gly<br>              1205                  1210                  1215 | 3648 |
| tcc ata ata cat gct gca ggt gtt gga gat att agc tgt atc ata cag<br>Ser Ile Ile His Ala Ala Gly Val Gly Asp Ile Ser Cys Ile Ile Gln<br>    1220                  1225                  1230 | 3696 |
| agg gat gaa ggg cgt gct cca atg agg cat tcc ttt cac tgg tca tct<br>Arg Asp Glu Gly Arg Ala Pro Met Arg His Ser Phe His Trp Ser Ser<br>1235                  1240                  1245 | 3744 |
| gaa aag cta tat tat gta gag gaa cca ttg ttg ctc cat ctt gaa cct<br>Glu Lys Leu Tyr Tyr Val Glu Glu Pro Leu Leu Leu His Leu Glu Pro<br>              1250                  1255                  1260 | 3792 |
| ccc cta tcc att tat ctt gaa ctg gac aag ctt aag tgc tat gaa aat<br>Pro Leu Ser Ile Tyr Leu Glu Leu Asp Lys Leu Lys Cys Tyr Glu Asn<br>1265                  1270                  1275                  1280 | 3840 |
| att cgc tat aca cca tcc cga gat cgt caa tgg cac ctc tac aca gtt<br>Ile Arg Tyr Thr Pro Ser Arg Asp Arg Gln Trp His Leu Tyr Thr Val<br>              1285                  1290                  1295 | 3888 |
| gtg gat acc aag cca caa cca att caa aga atg ttt ctt cga aca ctt<br>Val Asp Thr Lys Pro Gln Pro Ile Gln Arg Met Phe Leu Arg Thr Leu<br>    1300                  1305                  1310 | 3936 |
| atc aga cag cca acc aca aat gaa gga tac tct tct tat caa aga ctg<br>Ile Arg Gln Pro Thr Thr Asn Glu Gly Tyr Ser Ser Tyr Gln Arg Leu<br>1315                  1320                  1325 | 3984 |

| | |
|---|---|
| gat gca gaa acg tcc cgt acc caa ttg gct atg tct tat act tca agg<br>Asp Ala Glu Thr Ser Arg Thr Gln Leu Ala Met Ser Tyr Thr Ser Arg<br>　　　1330　　　　　　　　1335　　　　　　　　1340 | 4032 |
| agc att ttt agg tcc cta atg ggc gca atg gag gag ttg gaa ctt aac<br>Ser Ile Phe Arg Ser Leu Met Gly Ala Met Glu Glu Leu Glu Leu Asn<br>1345　　　　　　　　1350　　　　　　　　1355　　　　　　　　1360 | 4080 |
| tca cac aat acc acc atc aaa tct gaa cat gct cat atg tac ctc tat<br>Ser His Asn Thr Thr Ile Lys Ser Glu His Ala His Met Tyr Leu Tyr<br>　　　　　　　　1365　　　　　　　　1370　　　　　　　　1375 | 4128 |
| atc ata cgc gag cag caa ata gat gat ctt gtg cct tat tcc aag aaa<br>Ile Ile Arg Glu Gln Gln Ile Asp Asp Leu Val Pro Tyr Ser Lys Lys<br>　　　1380　　　　　　　　1385　　　　　　　　1390 | 4176 |
| att aac ata gaa gct ggc caa gaa gaa aca aca gtt gag gca atc ttg<br>Ile Asn Ile Glu Ala Gly Gln Glu Glu Thr Thr Val Glu Ala Ile Leu<br>　　　　　　　　1395　　　　　　　　1400　　　　　　　　1405 | 4224 |
| gaa gaa ctg gca cag gaa atc cat tcc tct gtt ggt gta aga atg cac<br>Glu Glu Leu Ala Gln Glu Ile His Ser Ser Val Gly Val Arg Met His<br>1410　　　　　　　　1415　　　　　　　　1420 | 4272 |
| aga tta ggc gtt ttc gtg tgg gaa atc aag ctc tgg att aca gca tgt<br>Arg Leu Gly Val Phe Val Trp Glu Ile Lys Leu Trp Ile Thr Ala Cys<br>1425　　　　　　　　1430　　　　　　　　1435　　　　　　　　1440 | 4320 |
| gga cag gca aat ggt gct tgg agg gtc att gta aac aat gtg act ggt<br>Gly Gln Ala Asn Gly Ala Trp Arg Val Ile Val Asn Asn Val Thr Gly<br>　　　　　　　　1445　　　　　　　　1450　　　　　　　　1455 | 4368 |
| cat aca tgc act gta cat ata tat cga gag atg gag gat gcc acc act<br>His Thr Cys Thr Val His Ile Tyr Arg Glu Met Glu Asp Ala Thr Thr<br>　　　1460　　　　　　　　1465　　　　　　　　1470 | 4416 |
| cat aaa gtg gtc tac agt tca gtc act gta aag ggt ccg ttg cat ggt<br>His Lys Val Val Tyr Ser Ser Val Thr Val Lys Gly Pro Leu His Gly<br>　　　　　　　　1475　　　　　　　　1480　　　　　　　　1485 | 4464 |
| gta ccg gtg aat gaa aac tat caa cct ttg gga ggt att gac cga aaa<br>Val Pro Val Asn Glu Asn Tyr Gln Pro Leu Gly Gly Ile Asp Arg Lys<br>1490　　　　　　　　1495　　　　　　　　1500 | 4512 |
| cgt ctt gca gcg aga aag aac agc acc aca tac tgc tat gat ttc ccc<br>Arg Leu Ala Ala Arg Lys Asn Ser Thr Thr Tyr Cys Tyr Asp Phe Pro<br>1505　　　　　　　　1510　　　　　　　　1515　　　　　　　　1520 | 4560 |
| ctt gca ttt caa aca tcc ttg gaa cag tcc tgg tca ata cag cag aca<br>Leu Ala Phe Gln Thr Ser Leu Glu Gln Ser Trp Ser Ile Gln Gln Thr<br>　　　　　　　　1525　　　　　　　　1530　　　　　　　　1535 | 4608 |
| gga att caa aga gct aat gat aag gat ctc cta aaa gta aca gag ctt<br>Gly Ile Gln Arg Ala Asn Asp Lys Asp Leu Leu Lys Val Thr Glu Leu<br>　　　1540　　　　　　　　1545　　　　　　　　1550 | 4656 |
| aaa ttt tcc gaa aaa gct ggt agt tgg ggt act tct ctt gtt cct gca<br>Lys Phe Ser Glu Lys Ala Gly Ser Trp Gly Thr Ser Leu Val Pro Ala<br>　　　　　　　　1555　　　　　　　　1560　　　　　　　　1565 | 4704 |
| gag cgt ctt cct gga ctc aat gat gtt ggc atg gta gcc tgg ttg atg<br>Glu Arg Leu Pro Gly Leu Asn Asp Val Gly Met Val Ala Trp Leu Met<br>1570　　　　　　　　1575　　　　　　　　1580 | 4752 |
| gaa atg tgt acg cct aaa ttc cca tct gga agg aca ata ttg gtt gtt<br>Glu Met Cys Thr Pro Lys Phe Pro Ser Gly Arg Thr Ile Leu Val Val<br>1585　　　　　　　　1590　　　　　　　　1595　　　　　　　　1600 | 4800 |
| tca aac gat gtg acc ttc aag gcc ggg tct ttt ggc cca aga gag gat<br>Ser Asn Asp Val Thr Phe Lys Ala Gly Ser Phe Gly Pro Arg Glu Asp<br>　　　　　　　　1605　　　　　　　　1610　　　　　　　　1615 | 4848 |
| gca ttc ttt aga gca gta act gat ctt gcc tgt gca aag aaa ata cct<br>Ala Phe Phe Arg Ala Val Thr Asp Leu Ala Cys Ala Lys Lys Ile Pro<br>　　　1620　　　　　　　　1625　　　　　　　　1630 | 4896 |
| tta att tac ttg gca gca aat tct ggt gcc cgt tta ggt gtt gcc gag<br>Leu Ile Tyr Leu Ala Ala Asn Ser Gly Ala Arg Leu Gly Val Ala Glu<br>　　　　　　　　1635　　　　　　　　1640　　　　　　　　1645 | 4944 |

```
gaa gtc aaa gct tgt ttc aaa gtt ggt tgg tct gag gaa tct aaa cct    4992
Glu Val Lys Ala Cys Phe Lys Val Gly Trp Ser Glu Glu Ser Lys Pro
    1650                1655                1660 gaa cat ggt ttt cag tat gta tat tta aca cct gag gat tat gct cga    5040
Glu His Gly Phe Gln Tyr Val Tyr Leu Thr Pro Glu Asp Tyr Ala Arg
1665                1670                1675                1680 atc gga tca tca gtg atg gca cat gaa tta aag ctt gaa agt gga gaa    5088
Ile Gly Ser Ser Val Met Ala His Glu Leu Lys Leu Glu Ser Gly Glu
                1685                1690                1695 acc aga tgg gtt ata gat acc att gtt ggc aaa gaa gat gga ctg gga    5136
Thr Arg Trp Val Ile Asp Thr Ile Val Gly Lys Glu Asp Gly Leu Gly
        1700                1705                1710 gtt gaa aac ttg agt ggt agt ggg gcc att gcc ggt gcc tat tca agg    5184
Val Glu Asn Leu Ser Gly Ser Gly Ala Ile Ala Gly Ala Tyr Ser Arg
    1715                1720                1725 gca tac aag gaa acc ttt aca ttg aca tat gtt acc ggt agg act gtt    5232
Ala Tyr Lys Glu Thr Phe Thr Leu Thr Tyr Val Thr Gly Arg Thr Val
    1730                1735                1740 gga att ggt gct tat ctt gct agg ctt ggg atg agg tgc ata cag agg    5280
Gly Ile Gly Ala Tyr Leu Ala Arg Leu Gly Met Arg Cys Ile Gln Arg
1745                1750                1755                1760 ctt gat caa cct ata att ctt acc ggg ttt tca gca tta aac aaa ctt    5328
Leu Asp Gln Pro Ile Ile Leu Thr Gly Phe Ser Ala Leu Asn Lys Leu
                1765                1770                1775 ctt ggt agg gag gtg tac agc tct cac atg caa ctt ggt gga ccg aaa    5376
Leu Gly Arg Glu Val Tyr Ser Ser His Met Gln Leu Gly Gly Pro Lys
        1780                1785                1790 atc atg gca aca aat gga gtc gtt cat ctc aca gtt tcg gac gac ctt    5424
Ile Met Ala Thr Asn Gly Val Val His Leu Thr Val Ser Asp Asp Leu
    1795                1800                1805 gaa ggc gtt tct tct att ttg aag tgg ctt agc tac gtt cct tct cat    5472
Glu Gly Val Ser Ser Ile Leu Lys Trp Leu Ser Tyr Val Pro Ser His
    1810                1815                1820 gta ggt ggt gca ctt ccc att gta aag ccc ctt gat ccc cca gag agg    5520
Val Gly Gly Ala Leu Pro Ile Val Lys Pro Leu Asp Pro Pro Glu Arg
1825                1830                1835                1840 gaa gtg gag tat tta ccg gaa aat tca tgc gat cct cgt gct gcc att    5568
Glu Val Glu Tyr Leu Pro Glu Asn Ser Cys Asp Pro Arg Ala Ala Ile
                1845                1850                1855 tcc gga act ctg gat gtt aat gga aag tgg ctg gga ggc att ttt gac    5616
Ser Gly Thr Leu Asp Val Asn Gly Lys Trp Leu Gly Gly Ile Phe Asp
        1860                1865                1870 aag gac agc ttt gtg gag aca cta gaa gga tgg gct aga aca gtt gtt    5664
Lys Asp Ser Phe Val Glu Thr Leu Glu Gly Trp Ala Arg Thr Val Val
    1875                1880                1885 aca gga agg gca aag ctt gga gga atc cct gtg gga att gtt gcg gtg    5712
Thr Gly Arg Ala Lys Leu Gly Gly Ile Pro Val Gly Ile Val Ala Val
    1890                1895                1900 gaa aca caa aca gtt atg caa ata ata cct gct gat cca ggt caa ctt    5760
Glu Thr Gln Thr Val Met Gln Ile Ile Pro Ala Asp Pro Gly Gln Leu
1905                1910                1915                1920 gat tct cac gag agg gtt gtt cct caa gcc ggg cag gtg tgg ttt cct    5808
Asp Ser His Glu Arg Val Val Pro Gln Ala Gly Gln Val Trp Phe Pro
                1925                1930                1935 gat tct gcg acc aag acg gcc caa gcg ata ttg gat ttc aac aga gaa    5856
Asp Ser Ala Thr Lys Thr Ala Gln Ala Ile Leu Asp Phe Asn Arg Glu
        1940                1945                1950 gaa ctc cca ctt ttc att atc gca aac tgg aga ggc ttt tca ggt gga    5904
Glu Leu Pro Leu Phe Ile Ile Ala Asn Trp Arg Gly Phe Ser Gly Gly
```

| | | | | | | | | | | | | | | | | |
|---|---|---|---|---|---|---|---|---|---|---|---|---|---|---|---|---|
| caa | agg | gac | ctt | ttt | gaa | gga | att | ctt | cag | gct | ggt | tcg | act | att | gtg | 5952 |
| Gln | Arg | Asp | Leu | Phe | Glu | Gly | Ile | Leu | Gln | Ala | Gly | Ser | Thr | Ile | Val | |
| | 1970 | | | | 1975 | | | | | 1980 | | | | | | |
| gag | aac | ctt | agg | aca | tac | aaa | cag | ccc | ata | ttt | gta | tac | att | cca | atg | 6000 |
| Glu | Asn | Leu | Arg | Thr | Tyr | Lys | Gln | Pro | Ile | Phe | Val | Tyr | Ile | Pro | Met | |
| 1985 | | | | | 1990 | | | | | 1995 | | | | | 2000 | |
| atg | ggt | gaa | ctc | cga | ggc | ggg | gct | tgg | gtt | gtt | gtc | gac | agc | cga | atc | 6048 |
| Met | Gly | Glu | Leu | Arg | Gly | Gly | Ala | Trp | Val | Val | Val | Asp | Ser | Arg | Ile | |
| | | | | 2005 | | | | | 2010 | | | | | 2015 | | |
| aac | tca | gac | cac | att | gaa | atg | tat | gct | gag | cga | acg | gcc | aaa | ggt | aac | 6096 |
| Asn | Ser | Asp | His | Ile | Glu | Met | Tyr | Ala | Glu | Arg | Thr | Ala | Lys | Gly | Asn | |
| | | | 2020 | | | | | 2025 | | | | | 2030 | | | |
| gtc | ctt | gag | ccg | gaa | gga | atg | att | gaa | atc | aaa | ttt | aga | aca | aga | gaa | 6144 |
| Val | Leu | Glu | Pro | Glu | Gly | Met | Ile | Glu | Ile | Lys | Phe | Arg | Thr | Arg | Glu | |
| | | 2035 | | | | | 2040 | | | | | 2045 | | | | |
| ttg | ttg | gag | tgt | atg | aga | aga | ctt | gat | caa | caa | ttg | att | aat | ttg | aag | 6192 |
| Leu | Leu | Glu | Cys | Met | Arg | Arg | Leu | Asp | Gln | Gln | Leu | Ile | Asn | Leu | Lys | |
| | | 2050 | | | | | 2055 | | | | | 2060 | | | | |
| gaa | aaa | ctt | tct | gaa | gcc | aag | agt | aac | aag | gac | tat | ggt | gca | tat | gat | 6240 |
| Glu | Lys | Leu | Ser | Glu | Ala | Lys | Ser | Asn | Lys | Asp | Tyr | Gly | Ala | Tyr | Asp | |
| 2065 | | | | | 2070 | | | | | 2075 | | | | | 2080 | |
| tct | ctg | cag | cag | cag | att | aga | ttc | cgt | gag | aaa | cag | ctt | ttg | cct | ttg | 6288 |
| Ser | Leu | Gln | Gln | Gln | Ile | Arg | Phe | Arg | Glu | Lys | Gln | Leu | Leu | Pro | Leu | |
| | | | | 2085 | | | | | 2090 | | | | | 2095 | | |
| tat | act | cag | ata | gct | aca | aaa | ttt | gct | gaa | ctc | cat | gat | act | tca | tta | 6336 |
| Tyr | Thr | Gln | Ile | Ala | Thr | Lys | Phe | Ala | Glu | Leu | His | Asp | Thr | Ser | Leu | |
| | | | | 2100 | | | | | 2105 | | | | | 2110 | | |
| aga | atg | aaa | gca | aag | ggt | gta | atc | aga | gaa | gtt | ctt | gat | tgg | cgt | aag | 6384 |
| Arg | Met | Lys | Ala | Lys | Gly | Val | Ile | Arg | Glu | Val | Leu | Asp | Trp | Arg | Lys | |
| | | | 2115 | | | | | 2120 | | | | | 2125 | | | |
| tcg | cgt | tct | gtc | ttc | tat | cag | aga | ctg | cac | agg | aga | atc | ggt | gag | cac | 6432 |
| Ser | Arg | Ser | Val | Phe | Tyr | Gln | Arg | Leu | His | Arg | Arg | Ile | Gly | Glu | His | |
| | | 2130 | | | | | 2135 | | | | | 2140 | | | | |
| tca | ctg | atc | aac | atc | gtg | aga | gat | gct | gct | ggt | gac | caa | ttg | tca | tat | 6480 |
| Ser | Leu | Ile | Asn | Ile | Val | Arg | Asp | Ala | Ala | Gly | Asp | Gln | Leu | Ser | Tyr | |
| 2145 | | | | | 2150 | | | | | 2155 | | | | | 2160 | |
| gtt | tct | gcc | atg | aac | ttg | ctc | aaa | gaa | tgg | tat | ctg | aat | tct | gat | atc | 6528 |
| Val | Ser | Ala | Met | Asn | Leu | Leu | Lys | Glu | Trp | Tyr | Leu | Asn | Ser | Asp | Ile | |
| | | | 2165 | | | | | 2170 | | | | | 2175 | | | |
| gcc | aaa | ggt | aga | gaa | gat | gct | tgg | ttg | gac | gat | gaa | gcc | ttc | ttc | aga | 6576 |
| Ala | Lys | Gly | Arg | Glu | Asp | Ala | Trp | Leu | Asp | Asp | Glu | Ala | Phe | Phe | Arg | |
| | | | 2180 | | | | | 2185 | | | | | 2190 | | | |
| tgg | agg | gat | gat | cca | gca | aac | tac | gag | gat | aaa | cta | aag | gaa | ttg | cgc | 6624 |
| Trp | Arg | Asp | Asp | Pro | Ala | Asn | Tyr | Glu | Asp | Lys | Leu | Lys | Glu | Leu | Arg | |
| | | | 2195 | | | | | 2200 | | | | | 2205 | | | |
| gtc | cag | aga | ctg | ttg | ctt | cag | ttg | aca | aat | att | ggc | gac | tcg | gct | cta | 6672 |
| Val | Gln | Arg | Leu | Leu | Leu | Gln | Leu | Thr | Asn | Ile | Gly | Asp | Ser | Ala | Leu | |
| | | 2210 | | | | | 2215 | | | | | 2220 | | | | |
| gat | tta | caa | gct | cta | cct | caa | ggt | ctt | gcc | gcc | ctt | tta | agc | aag | ttg | 6720 |
| Asp | Leu | Gln | Ala | Leu | Pro | Gln | Gly | Leu | Ala | Ala | Leu | Leu | Ser | Lys | Leu | |
| 2225 | | | | | 2230 | | | | | 2235 | | | | | 2240 | |
| gaa | gca | tca | agt | cgc | gat | aag | ttg | atc | agt | gaa | ctt | cgc | aaa | gta | ctc | 6768 |
| Glu | Ala | Ser | Ser | Arg | Asp | Lys | Leu | Ile | Ser | Glu | Leu | Arg | Lys | Val | Leu | |
| | | | | 2245 | | | | | 2250 | | | | | 2255 | | |
| ggt | tagtagacag | tgaatgctcc | tgtgatctgc | ccatgcactc | atgttgtagt | | | | | | | | | | | 6821 |
| Gly | | | | | | | | | | | | | | | | | gttcacgtcg ttgatacatg accatataga aatgtatcca ttttacgatg ttatcatcaa     6881

-continued

```
agtagcagca tccctcggaa aatggacttt cacttgaggg atcaactgta aatgacttcg    6941
gtcttggata gatatttaat ttatgcagtt agaggatcat aaccagcatc accatgtttg    7001
gtctatttat ttgctggttg attgattctt tgcgtgtatc tgaataaaca tgtaataatt    7061
tgtaacattg attatttttt atgaaaaaca aagttttggg cactccttt ataaaaaaaa    7121 aaaaagaat tcctgcagcc cggggatcc                                      7151
```

<210> SEQ ID NO 8
<211> LENGTH: 2257
<212> TYPE: PRT
<213> ORGANISM: Medicago sativa

<400> SEQUENCE: 8

```
Met Ala Ser Val Gly Arg Gly Asn Gly Tyr Leu Asn Ser Val Leu Pro
  1               5                  10                  15

Ser Arg His Pro Ala Thr Thr Thr Glu Val Asp Glu Tyr Cys Asn Ala
             20                  25                  30

Leu Gly Gly Asn Lys Pro Ile His Ser Ile Leu Ile Ala Asn Asn Gly
         35                  40                  45

Met Ala Ala Val Lys Phe Ile Arg Ser Val Arg Ser Trp Ala Tyr Glu
     50                  55                  60

Thr Phe Gly Thr Glu Lys Ala Ile Leu Leu Val Ala Met Ala Thr Pro
 65                  70                  75                  80

Glu Asp Met Arg Ile Asn Ala Glu His Ile Arg Ile Ala Asp Gln Phe
                 85                  90                  95

Val Glu Val Pro Gly Gly Thr Asn Asn Asn Tyr Ala Asn Val Gln
            100                 105                 110

Leu Ile Leu Glu Ile Ala Glu Ile Thr His Val Asp Ala Val Trp Pro
        115                 120                 125

Gly Trp Gly His Ala Ser Glu Asn Pro Glu Leu Pro Asp Ala Leu Lys
    130                 135                 140

Ala Lys Gly Ile Val Phe Leu Gly Pro Pro Ala Ile Ser Met Ala Ala
145                 150                 155                 160

Leu Gly Asp Lys Ile Gly Ser Ser Leu Ile Ala Gln Ala Ala Glu Val
                165                 170                 175

Pro Thr Leu Pro Trp Ser Gly Ser His Val Lys Ile Pro Pro Glu Ser
            180                 185                 190

Asp Leu Ile Thr Ile Pro Asp Glu Ile Tyr Arg Ala Ala Cys Val Tyr
        195                 200                 205

Thr Thr Glu Glu Ala Ile Ala Ser Cys Gln Val Val Gly Tyr Pro Ala
    210                 215                 220

Met Ile Lys Ala Ser Trp Gly Gly Gly Gly Lys Gly Ile Arg Lys Val
225                 230                 235                 240

His Asn Asp Asp Glu Val Arg Ala Leu Phe Lys Gln Val Gln Gly Glu
                245                 250                 255

Val Pro Gly Ser Pro Ile Phe Ile Met Lys Val Ala Ser Gln Ser Arg
            260                 265                 270

His Leu Glu Val Gln Leu Ile Cys Asp Gln His Gly Asn Phe Ala Ala
        275                 280                 285

Leu His Ser Arg Asp Cys Ser Val Gln Arg Arg His Gln Lys Ile Ile
    290                 295                 300

Glu Glu Gly Pro Ile Thr Val Ala Pro Pro Glu Thr Val Lys Glu Leu
305                 310                 315                 320

Glu Gln Ala Ala Arg Arg Leu Ala Lys Ser Val Asn Tyr Val Gly Ala
```

-continued

```
                    325                 330                 335
Ala Thr Val Glu Tyr Leu Tyr Ser Met Glu Thr Gly Glu Tyr Tyr Phe
                340                 345                 350
Leu Glu Leu Asn Pro Arg Leu Gln Val Glu His Pro Val Thr Glu Trp
                355                 360                 365
Ile Ala Glu Ile Asn Leu Pro Ala Ala Gln Val Ala Val Gly Met Gly
            370                 375                 380
Ile Pro Leu Trp Gln Ile Pro Glu Ile Arg Arg Phe Tyr Gly Met Glu
385                 390                 395                 400
His Gly Gly Gly Asn Asp Gly Trp Lys Lys Thr Ser Val Leu Ala Thr
                405                 410                 415
Pro Phe Asp Phe Asp Glu Ala Gln Ser Thr Lys Pro Lys Gly His Cys
            420                 425                 430
Val Ala Val Arg Val Thr Ser Glu Asp Pro Asp Gly Phe Thr Pro
            435                 440                 445
Thr Gly Gly Lys Val Gln Glu Leu Ser Phe Lys Ser Lys Pro Asn Val
        450                 455                 460
Trp Ala Tyr Phe Ser Val Lys Ser Gly Gly Ile His Glu Phe Ser
465                 470                 475                 480
Asp Ser Gln Phe Gly His Val Phe Ala Phe Gly Glu Ser Arg Ala Leu
                485                 490                 495
Ala Ile Ala Asn Met Val Leu Gly Leu Lys Glu Ile Gln Ile Arg Gly
                500                 505                 510
Glu Ile Arg Thr Asn Val Asp Tyr Thr Ile Asp Leu Leu Asn Ala Ser
            515                 520                 525
Asp Tyr Arg Asp Asn Lys Ile His Thr Gly Trp Leu Asp Ser Arg Ile
            530                 535                 540
Ala Met Arg Val Arg Ala Glu Arg Pro Pro Trp Tyr Leu Ser Val Val
545                 550                 555                 560
Gly Gly Ala Leu Tyr Lys Ala Ser Ala Ser Ser Ala Ala Leu Val Ser
                565                 570                 575
Asp Tyr Val Gly Tyr Leu Glu Lys Gly Gln Ile Pro Pro Lys His Ile
            580                 585                 590
Ser Leu Val His Ser Gln Val Ser Leu Ser Ile Glu Gly Ser Lys Tyr
            595                 600                 605
Thr Ile Asp Met Val Arg Gly Gly Pro Gly Ser Tyr Lys Leu Lys Leu
        610                 615                 620
Asn Gln Ser Glu Ile Glu Ala Glu Ile His Thr Leu Arg Asp Gly Gly
625                 630                 635                 640
Leu Leu Met Gln Leu Asp Gly Asn Ser His Val Ile Tyr Ala Glu Glu
                645                 650                 655
Glu Ala Ala Gly Thr Arg Leu Leu Ile Asp Gly Arg Thr Cys Leu Leu
                660                 665                 670
Gln Asn Asp Asp Asp Pro Ser Lys Leu Ile Gly Glu Thr Pro Cys Lys
            675                 680                 685
Leu Leu Arg Tyr Leu Val Ala Asp Asp Ser Gln Ile Asp Ala Asp Thr
        690                 695                 700
Pro Tyr Ala Glu Val Glu Val Met Lys Met Cys Met Pro Leu Leu Ser
705                 710                 715                 720
Pro Ala Ser Gly Ile Ile His Phe Arg Met Ala Glu Gly Gln Ala Met
                725                 730                 735
Gln Ala Gly Glu Leu Ile Ala Lys Leu Asp Leu Asp Asp Gly Ser Ala
                740                 745                 750
```

-continued

Val Arg Lys Ala Glu Pro Phe Thr Gly Ser Phe Pro Ile Leu Gly Pro
        755                 760                 765

Pro Thr Ala Ile Ser Gly Lys Val His Gln Lys Cys Ala Ala Ser Leu
        770                 775                 780

Asn Ala Ala Arg Met Ile Leu Ala Gly Tyr Glu His Asn Ile Asp Glu
785                 790                 795                 800

Val Val Val Lys Ser Leu Leu Asn Cys Leu Asp Ser Pro Glu Leu Pro
                805                 810                 815

Phe Leu Gln Trp Gln Glu Cys Phe Ala Val Leu Ala Thr Arg Leu Pro
                820                 825                 830

Lys Asp Leu Arg Asn Glu Leu Glu Ala Lys Tyr Lys Glu Phe Glu Ile
                835                 840                 845

Ile Ser Ser Ser Gln Thr Ile Asp Phe Pro Ala Lys Leu Leu Lys Ala
        850                 855                 860

Ile Leu Glu Ala His Leu Ser Ser Cys Pro Glu Asn Glu Lys Gly Ala
865                 870                 875                 880

Leu Glu Arg Leu Val Glu Pro Leu Thr Ser Leu Val Lys Ser Tyr Glu
                885                 890                 895

Gly Gly Arg Glu Ser His Ala His Lys Ile Val Gln Ser Leu Phe Glu
                900                 905                 910

Glu Tyr Leu Ser Val Glu Glu Leu Phe Ser Asp Asn Ile Gln Ala Asp
        915                 920                 925

Val Ile Glu Arg Leu Arg Leu Gln Tyr Lys Lys Asp Leu Leu Lys Ile
        930                 935                 940

Val Asp Ile Val Leu Ser His Gln Gly Val Lys Ser Lys Asn Lys Leu
945                 950                 955                 960

Ile Leu Arg Leu Met Asp Lys Leu Val Tyr Pro Asn Pro Ala Ala Tyr
                965                 970                 975

Arg Asp Gln Leu Ile Arg Phe Ser Gln Leu Asn His Ile Val Tyr Ser
                980                 985                 990

Glu Leu Ala Leu Lys Ala Ser Gln Leu Leu Glu Gln Thr Lys Leu Ser
        995                 1000                1005

Glu Leu Arg Ser Ser Ile Ala Arg Ser Leu Ser Glu Leu Glu Met Phe
1010                1015                1020

Thr Glu Asp Gly Glu Asn Ile Asp Thr Pro Lys Arg Lys Ser Ala Ile
1025                1030                1035                1040

Asn Asp Arg Met Glu Asp Leu Val Ser Ala Pro Leu Ala Val Glu Asp
                1045                1050                1055

Ala Leu Val Gly Leu Phe Asp His Ser Asp His Thr Leu Gln Arg Arg
                1060                1065                1070

Val Val Glu Thr Tyr Ile Arg Arg Leu Tyr Gln Pro Tyr Leu Val Lys
        1075                1080                1085

Asp Ser Ile Arg Met Gln Trp His Arg Ser Gly Leu Ile Ala Thr Trp
        1090                1095                1100

Glu Phe Leu Glu Glu Tyr Val Arg Lys Asn Gly Val Glu Asp Lys
1105                1110                1115                1120

Thr Leu Val Glu Lys His Ser Glu Lys Lys Trp Gly Val Met Val Val
                1125                1130                1135

Ile Lys Ser Leu Gln Phe Leu Pro Ala Ile Ile Ser Ala Ala Leu Arg
                1140                1145                1150

Glu Ala Thr Asn Asn Phe His Asp Pro Leu Lys Ser Gly Ser Gly Asp
        1155                1160                1165

```
Ser Ser Asn His Gly Asn Met Met His Ile Gly Leu Val Gly Ile Asn
    1170                1175                1180
Asn Gln Met Ser Leu Leu Gln Asp Ser Gly Asp Glu Asp Gln Ala Gln
1185                1190                1195                1200
Glu Arg Ile Asp Lys Leu Ala Lys Ile Leu Arg Glu Gln Glu Ile Gly
                1205                1210                1215
Ser Ile Ile His Ala Ala Gly Val Gly Asp Ile Ser Cys Ile Ile Gln
    1220                1225                1230
Arg Asp Glu Gly Arg Ala Pro Met Arg His Ser Phe His Trp Ser Ser
            1235                1240                1245
Glu Lys Leu Tyr Tyr Val Glu Glu Pro Leu Leu His Leu Glu Pro
    1250                1255                1260
Pro Leu Ser Ile Tyr Leu Glu Leu Asp Lys Leu Lys Cys Tyr Glu Asn
1265                1270                1275                1280
Ile Arg Tyr Thr Pro Ser Arg Asp Arg Gln Trp His Leu Tyr Thr Val
                1285                1290                1295
Val Asp Thr Lys Pro Gln Pro Ile Gln Arg Met Phe Leu Arg Thr Leu
            1300                1305                1310
Ile Arg Gln Pro Thr Thr Asn Glu Gly Tyr Ser Ser Tyr Gln Arg Leu
    1315                1320                1325
Asp Ala Glu Thr Ser Arg Thr Gln Leu Ala Met Ser Tyr Thr Ser Arg
    1330                1335                1340
Ser Ile Phe Arg Ser Leu Met Gly Ala Met Glu Glu Leu Glu Leu Asn
1345                1350                1355                1360
Ser His Asn Thr Thr Ile Lys Ser Glu His Ala His Met Tyr Leu Tyr
                1365                1370                1375
Ile Ile Arg Glu Gln Gln Ile Asp Asp Leu Val Pro Tyr Ser Lys Lys
            1380                1385                1390
Ile Asn Ile Glu Ala Gly Gln Glu Glu Thr Thr Val Glu Ala Ile Leu
    1395                1400                1405
Glu Glu Leu Ala Gln Glu Ile His Ser Ser Val Gly Val Arg Met His
    1410                1415                1420
Arg Leu Gly Val Phe Val Trp Glu Ile Lys Leu Trp Ile Thr Ala Cys
1425                1430                1435                1440
Gly Gln Ala Asn Gly Ala Trp Arg Val Ile Val Asn Asn Val Thr Gly
                1445                1450                1455
His Thr Cys Thr Val His Ile Tyr Arg Glu Met Glu Asp Ala Thr Thr
            1460                1465                1470
His Lys Val Val Tyr Ser Ser Val Thr Val Lys Gly Pro Leu His Gly
    1475                1480                1485
Val Pro Val Asn Glu Asn Tyr Gln Pro Leu Gly Gly Ile Asp Arg Lys
    1490                1495                1500
Arg Leu Ala Ala Arg Lys Asn Ser Thr Thr Tyr Cys Tyr Asp Phe Pro
1505                1510                1515                1520
Leu Ala Phe Gln Thr Ser Leu Glu Gln Ser Trp Ser Ile Gln Gln Thr
                1525                1530                1535
Gly Ile Gln Arg Ala Asn Asp Lys Asp Leu Leu Lys Val Thr Glu Leu
            1540                1545                1550
Lys Phe Ser Glu Lys Ala Gly Ser Trp Gly Thr Ser Leu Val Pro Ala
    1555                1560                1565
Glu Arg Leu Pro Gly Leu Asn Asp Val Gly Met Val Ala Trp Leu Met
    1570                1575                1580
Glu Met Cys Thr Pro Lys Phe Pro Ser Gly Arg Thr Ile Leu Val Val
```

-continued

```
1585                1590                1595                1600

Ser Asn Asp Val Thr Phe Lys Ala Gly Ser Phe Gly Pro Arg Glu Asp
                1605                1610                1615

Ala Phe Phe Arg Ala Val Thr Asp Leu Ala Cys Ala Lys Lys Ile Pro
            1620                1625                1630

Leu Ile Tyr Leu Ala Ala Asn Ser Gly Ala Arg Leu Gly Val Ala Glu
        1635                1640                1645

Glu Val Lys Ala Cys Phe Lys Val Gly Trp Ser Glu Ser Lys Pro
    1650                1655                1660

Glu His Gly Phe Gln Tyr Val Tyr Leu Thr Pro Glu Asp Tyr Ala Arg
1665                1670                1675                1680

Ile Gly Ser Ser Val Met Ala His Glu Leu Lys Leu Glu Ser Gly Glu
                1685                1690                1695

Thr Arg Trp Val Ile Asp Thr Ile Val Gly Lys Glu Asp Gly Leu Gly
                1700                1705                1710

Val Glu Asn Leu Ser Gly Ser Gly Ala Ile Ala Gly Ala Tyr Ser Arg
            1715                1720                1725

Ala Tyr Lys Glu Thr Phe Thr Leu Thr Tyr Val Thr Gly Arg Thr Val
        1730                1735                1740

Gly Ile Gly Ala Tyr Leu Ala Arg Leu Gly Met Arg Cys Ile Gln Arg
1745                1750                1755                1760

Leu Asp Gln Pro Ile Ile Leu Thr Gly Phe Ser Ala Leu Asn Lys Leu
                1765                1770                1775

Leu Gly Arg Glu Val Tyr Ser Ser His Met Gln Leu Gly Gly Pro Lys
            1780                1785                1790

Ile Met Ala Thr Asn Gly Val Val His Leu Thr Val Ser Asp Asp Leu
        1795                1800                1805

Glu Gly Val Ser Ser Ile Leu Lys Trp Leu Ser Tyr Val Pro Ser His
    1810                1815                1820

Val Gly Gly Ala Leu Pro Ile Val Lys Pro Leu Asp Pro Glu Arg
1825                1830                1835                1840

Glu Val Glu Tyr Leu Pro Glu Asn Ser Cys Asp Pro Arg Ala Ala Ile
                1845                1850                1855

Ser Gly Thr Leu Asp Val Asn Gly Lys Trp Leu Gly Gly Ile Phe Asp
            1860                1865                1870

Lys Asp Ser Phe Val Glu Thr Leu Glu Gly Trp Ala Arg Thr Val Val
        1875                1880                1885

Thr Gly Arg Ala Lys Leu Gly Gly Ile Pro Val Gly Ile Val Ala Val
    1890                1895                1900

Glu Thr Gln Thr Val Met Gln Ile Ile Pro Ala Asp Pro Gly Gln Leu
1905                1910                1915                1920

Asp Ser His Glu Arg Val Val Pro Gln Ala Gly Gln Val Trp Phe Pro
                1925                1930                1935

Asp Ser Ala Thr Lys Thr Ala Gln Ala Ile Leu Asp Phe Asn Arg Glu
            1940                1945                1950

Glu Leu Pro Leu Phe Ile Ile Ala Asn Trp Arg Gly Phe Ser Gly Gly
        1955                1960                1965

Gln Arg Asp Leu Phe Glu Gly Ile Leu Gln Ala Gly Ser Thr Ile Val
    1970                1975                1980

Glu Asn Leu Arg Thr Tyr Lys Gln Pro Ile Phe Val Tyr Ile Pro Met
1985                1990                1995                2000

Met Gly Glu Leu Arg Gly Gly Ala Trp Val Val Val Asp Ser Arg Ile
                2005                2010                2015
```

Asn Ser Asp His Ile Glu Met Tyr Ala Glu Arg Thr Ala Lys Gly Asn
            2020                2025                2030

Val Leu Glu Pro Glu Gly Met Ile Glu Ile Lys Phe Arg Thr Arg Glu
            2035                2040                2045

Leu Leu Glu Cys Met Arg Arg Leu Asp Gln Gln Leu Ile Asn Leu Lys
            2050                2055                2060

Glu Lys Leu Ser Glu Ala Lys Ser Asn Lys Asp Tyr Gly Ala Tyr Asp
2065                2070                2075                2080

Ser Leu Gln Gln Gln Ile Arg Phe Arg Glu Lys Gln Leu Leu Pro Leu
            2085                2090                2095

Tyr Thr Gln Ile Ala Thr Lys Phe Ala Glu Leu His Asp Thr Ser Leu
            2100                2105                2110

Arg Met Lys Ala Lys Gly Val Ile Arg Glu Val Leu Asp Trp Arg Lys
            2115                2120                2125

Ser Arg Ser Val Phe Tyr Gln Arg Leu His Arg Ile Gly Glu His
            2130                2135                2140

Ser Leu Ile Asn Ile Val Arg Asp Ala Ala Gly Asp Gln Leu Ser Tyr
2145                2150                2155                2160

Val Ser Ala Met Asn Leu Leu Lys Glu Trp Tyr Leu Asn Ser Asp Ile
            2165                2170                2175

Ala Lys Gly Arg Glu Asp Ala Trp Leu Asp Asp Glu Ala Phe Phe Arg
            2180                2185                2190

Trp Arg Asp Asp Pro Ala Asn Tyr Glu Asp Lys Leu Lys Glu Leu Arg
            2195                2200                2205

Val Gln Arg Leu Leu Leu Gln Leu Thr Asn Ile Gly Asp Ser Ala Leu
            2210                2215                2220

Asp Leu Gln Ala Leu Pro Gln Gly Leu Ala Ala Leu Leu Ser Lys Leu
2225                2230                2235                2240

Glu Ala Ser Ser Arg Asp Lys Leu Ile Ser Glu Leu Arg Lys Val Leu
            2245                2250                2255

Gly

<210> SEQ ID NO 9
<211> LENGTH: 20
<212> TYPE: DNA
<213> ORGANISM: Artificial Sequence
<220> FEATURE:
<223> OTHER INFORMATION: primer for PCR

<400> SEQUENCE: 9
gtaggcaccc tgctactaca                                           20

<210> SEQ ID NO 10
<211> LENGTH: 23
<212> TYPE: DNA
<213> ORGANISM: Artificial Sequence
<220> FEATURE:
<223> OTHER INFORMATION: primer for PCR

<400> SEQUENCE: 10
catcaggaat agtaatcaag tca                                       23

<210> SEQ ID NO 11
<211> LENGTH: 46
<212> TYPE: DNA
<213> ORGANISM: Artificial Sequence
<220> FEATURE:
<223> OTHER INFORMATION: representative construct (3' end)

-continued

```
<400> SEQUENCE: 11
ccttttataa aaaaaaaaaa aagaattcct gcagcccggg ggatcc                46

<210> SEQ ID NO 12
<211> LENGTH: 46
<212> TYPE: DNA
<213> ORGANISM: Artificial Sequence
<220> FEATURE:
<223> OTHER INFORMATION: representative construct (3' end)

<400> SEQUENCE: 12
ccttttataa aaaaaaaaaa aagaattcct gcagcccggg ggatcc                46
```